United States Patent [19]
Lashmore et al.

[11] Patent Number: 6,001,289
[45] Date of Patent: Dec. 14, 1999

[54] ACID ASSISTED COLD WELDING AND INTERMETALLIC FORMATION

[75] Inventors: David S. Lashmore, Lebanon, N.H.; Moshe P. Dariel, Rockville, Md.; Christian E. Johnson, Middletown, Md.; Menahem B. Ratzker, Silver Spring, Md.; Anthony A. Guiseppetti, Frederick, Md.; Frederick C. Eichmiller, Ijamsville, Md.; Glenn L. Beane, Plymouth, N.H.; David R. Kelley, Martinsburg, W. Va.

[73] Assignee: Materials Innovation, Inc., West Lebanon, N.H.

[21] Appl. No.: 08/317,729

[22] Filed: Oct. 4, 1994

Related U.S. Application Data

[63] Continuation-in-part of application No. 08/133,316, Oct. 8, 1993, abandoned, which is a continuation-in-part of application No. 07/802,420, Dec. 4, 1991, Pat. No. 5,318,746.

[51] Int. Cl.$^6$ ................. B27N 3/02; B22F 1/04; B05D 3/10; B05D 1/18
[52] U.S. Cl. ............ 264/109; 427/216; 427/217; 427/309; 427/436; 419/35; 419/64; 419/66
[58] Field of Search .................... 427/216, 217, 427/309, 436, 443.2; 420/526; 419/35, 64, 66; 264/109

[56] References Cited

U.S. PATENT DOCUMENTS

| | | | |
|---|---|---|---|
| Re. 29,093 | 12/1976 | Burns | 264/111 |
| 3,004,332 | 10/1961 | Werner | 29/182.5 |

(List continued on next page.)

FOREIGN PATENT DOCUMENTS

| | | | |
|---|---|---|---|
| 0291944 | 11/1988 | European Pat. Off. | A61K 6/04 |
| 2 216 545 | 10/1989 | United Kingdom | B22F 3/16 |

OTHER PUBLICATIONS

Horibe, et al., "Gallium Alloys for Dental Restoration", *J. Fukuoka Dent. Coll.*, 12(4):198–204, 1986, p. 33.

Joujima, H., et al., "Studies on Biological Evaluation of Gallium Alloy", *J. Fukuoka Dent. Coll.*, 14(3):249–257, 1987, p. 40.

Yoshida, et al., "The Basic Study on Galliuim Alloy for Restoration", *J. Fukuoka Dent. Coll.*, 31(4):1004–1012, 1988, pp. 1004–1005.

Greener, et al., "Dental Amalgams", *Dental Materials: Properties and Selection*, Quintessence Publishing Co., Inc., 1989, pp. 263–281.

Masuhara, et al., Study on Toxicity of a New Gallium Alloy for Dental Restorations, *Journal of Dental Health*, 27, p. 361, (1987).

(List continued on next page.)

*Primary Examiner*—Shrive Beck
*Assistant Examiner*—Michael Barr
*Attorney, Agent, or Firm*—Fran S. Wasserman

[57] ABSTRACT

A metallic composite solid, containing alloys and/or intermetallics, is formed by compacting at moderate pressure a mixture of powder particles, foils or sheets at a temperature close to room temperature, well below the melting temperature of the constituent components and without the addition of low melting metals such as mercury, indium or gallium acting as a sintering agent. This low temperature consolidation of the powder mixture is enhanced by having the surface oxide of the powder particles removed, prior to consolidation, and/or by coating the particles with an oxide-replacing metal such as silver or gold. The coating process may be replacement reactions, autocatalytic reduction or electrolytic reduction. The composite formation is assisted by the addition of a liquid acid such as fluoroboric acid, sulfuric acid, fluoric acid, adipic acid, ascorbic acid, or nitric acid. A preferred embodiment of the process for metal solid composite formation is a process for forming dental restorative materials at ambient temperatures and under pressure exerted by manual dental instrumentation.

24 Claims, 15 Drawing Sheets

U.S. PATENT DOCUMENTS

| | | | |
|---|---|---|---|
| 3,914,507 | 10/1975 | Fustukian | 428/404 |
| 3,933,961 | 1/1976 | Burns | 264/111 |
| 4,181,757 | 1/1980 | Youdelis | 427/229 |
| 4,218,507 | 8/1980 | Deffeyes et al. | 428/328 |
| 4,323,395 | 4/1982 | Li | 75/212 |
| 4,426,404 | 1/1984 | Shoher et al. | 427/2 |
| 4,427,501 | 1/1984 | Rogers | 204/37 R |
| 4,450,188 | 5/1984 | Kawasumi | 427/217 |
| 4,528,207 | 7/1985 | Johnson | 427/3 |
| 4,664,855 | 5/1987 | Tremblay et al. | 264/11 |
| 4,742,861 | 5/1988 | Shoher et al. | 164/80 |
| 4,859,412 | 8/1989 | Groll et al. | 419/23 |
| 4,963,184 | 10/1990 | Diehl et al. | 75/247 |
| 4,970,050 | 11/1990 | Groll et al. | 419/36 |
| 4,990,394 | 2/1991 | Shoher et al. | 428/212 |
| 4,997,699 | 3/1991 | Shoher et al. | 428/212 |
| 5,064,690 | 11/1991 | Sando et al. | 427/215 |
| 5,118,317 | 6/1992 | Wijnen | 415/50 |
| 5,183,631 | 2/1993 | Kugimiya et al. | 419/10 |
| 5,276,290 | 1/1994 | Bladon | 174/262 |
| 5,302,464 | 4/1994 | Nomura et al. | 428/551 |
| 5,334,240 | 8/1994 | Ferrier | 106/1.22 |

OTHER PUBLICATIONS

Kim, et al., The Clinical Observation of Gallium Alloy as a New Dental Restorative Material for Primary Teeth, *J. Fukuoka Dent. Coll.*, 14(4):395–400, 1988, p. 56.

S. R. Natarajan, et al., "Electroplating Baths for Silver—A review of Cyanide–Free Formulations", *Metal Finishing*, Feb. 1971, pp. 51–56.

Fackelma, "Can Dental Fillings Create Drug Resistance", *Science News*, Apr. 1993.

20 µm

20 μm

20 μm

100 μm

ACID ASSISTED COLD WELDING AND INTERMETALLIC FORMATION

This application is a continuation-in-part of U.S. patent application Ser. No. 08/133,316, filed Oct. 8, 1993 abandoned, which is in turn a continuation-in-part of U.S. patent application Ser. No. 07/802,420, filed Dec. 4, 1991, which issued on Jun. 7, 1994 as U.S. Pat. No. 5,318,746.

FIELD OF INVENTION

The invention relates to a process of consolidating metallic and intermetallic composite materials and a process of forming bulk intermetallics at ambient temperatures. In preferred embodiments, the invention relates to processes for forming the metallic composite materials as in situ dental restorations, high temperature materials, copper-tungsten and similar materials for thermal management, aluminides such as nickel aluminides, nickel titanium alloys for shape memory effects applications and titanium nickel tin alloys.

BACKGROUND

Powder metallurgy is a processing technique whereby very small diameter powder particles are compressed into parts or shapes by a number of methods that include vacuum hot pressing, hot isostatic pressing (HIP), sinter hipping, hot forging, etc. These processes require the sequential or simultaneous application of high temperature and pressure. Typically, the temperatures used in powder metallurgy are at an appreciable fraction of the melting point ($T_m$) of the compressed elements or alloys, usually above 0.8 $T_m$. The pressures applied are often near or beyond the yield point of the metals involved. In the case of metal foils or sheets, consolidation is often done by hot roll bonding. One of the reasons for these severe conditions results from the need to break up the naturally occurring oxide on the surface of the material, thereby enabling the surfaces of the powder particles (foils or sheets) to weld together at a sufficient number of contact points so as to provide adequate adhesion between the individual particles, sheets or foils.

Powder metallurgy is useful as an alternative to comelting appropriate amounts of metal constituent components in forming intermetallic compounds. Intermetallic compounds have a great potential for a variety of applications as a result of their specific properties such as hardness, high elastic moduli and oxidation resistance. On the other hand, the inherent brittleness of intermetallic compounds severely curtails their use in conventional thermomechanical processing operations to form net shapes. As an alternative, powder technology is often used for processing intermetallic compounds. The starting materials for this approach are pre-alloyed compounds that have been comminuted by various methods into powder particles. The limitation of this approach is that it relies on compaction of powders which are inherently brittle and do not deform with ease. Compound formation, however, may also take place by solid state interdiffusion of mostly ductile constituent elements which can be compacted with relative ease. Mixtures of elemental metal powders, maintained in close mutual contact for a sufficient length of time at the appropriate temperature, interdiffuse and form intermetallic compounds. In some situations, intermetallic compound formation is required, but exposure to elevated temperature has to be limited or avoided. An example of such a situation may be the requirement for compound formation (for protheses or as dental restorative material) in a human body environment.

Intermetallic compound formation by interdiffusion of the constituent elements or extremely finely divided multi-phase solid formation by non-compound forming and non-interdiffusing elements is favored when the starting materials are in the form of a very small size particle powder. Such powders possess a large specific surface area, and hence, when mixed, form a relatively large interface area between the different constituents. The generation of an interface area between the different constituents depends on the efficiency of the mixing technique and also on the nature and properties of the mixed powder particles.

Several mixing techniques are commonly used in order to maximize the contact points (interface area) between particles of different kinds. If the effect of particle properties on the outcome of the mixing process is neglected, prolonged mixing will tend to maximize the number of contact points between different particles by striving towards a random distribution of the particles of different kind. Many particle properties such as particle size and shape, surface roughness, in addition to electrostatic phenomena, promote segregation effects and thus reduce and curtail the homogeneous mixing of different powders. Thus, multimodal particle size distribution favors space filling and increased density but also favors particle segregation. The most commonly used mixing technique relies on the tumbling-type blending of the powders. Ball milling is another technique that is used for mixing and also for reducing particle size. An extension of ball-milling is the mechanical alloying technique that yields alloyed powder products from elemental powder mixtures. Alloy or compound formation by ball milling is dependent on the kinetic energy input due to the rapidly rotating hard balls impinging on the powder particles. Thus ball-milling leads to high local temperature increases.

Intermetallic compound formation at the interface of two metals in intimate contact is a documented phenomenon. In some instances, the formation of intermetallic compounds is beneficial, in others, its effects may be detrimental. The formation of a new compound at temperatures below the melting point of the metals in contact relies on interdiffusion effects in the solid state. In most binary combinations, ambient temperature is well below the melting temperature of the constituent metals and, consequently, little or no compound formation takes place at the interface. Notable exceptions to this are diffusion couples in which one of the constituent metals, e.g. mercury or gallium, has a low melting point, below or close to room temperature. Another important group of binary combinations which shows room temperature compound formation, consists of a group I-B of the periodic table (Cu, Ag or Au) metal juxtaposed to a group III-A or IV-A (In, Sn or Pb) element. K. N. Tu et al., *Jap. J. Appl. Phys. Suppl.*, Pt.1, 633 (1974). It is believed that room temperature compound formation in these systems is related to fast diffusion behavior of the noble or near noble component (the I-B elements) in the matrices of the group III-A or IV-A metals. A. D. LeClaire, *J. Nucl. Mat.* 69 & 70, 70 (1978). Fast diffusion occurs by virtue of the interstitial or partly interstitial diffusivity of the fast diffusing components, W. K. Warburton et al., "Diffusion in Solids, Recent Developments", Nowick and Burton (eds.), Academic Press, New York, 1975, p.172. It is noteworthy that interfaces between two components, each of which respectively belongs to one ot the two classes previously defined, are of common occurrence in electronic devices and it is not surprising, therefore, that such systems have been subject to relatively close scrutiny over the past years K. N. Tu, *Ann. Rev. Mater. Sci.*, 15, 147 (1985). The quasi-totality of the room temperature intermetallic compound formation studies in these systems has made use of the thin film configuration. This configuration yields samples with a high interface to total volume ratio permitting effective study of compound formation at the interface. The phase diagrams in most binary combinations of this kind show the presence at room temperature of several equilibrium intermetallic compounds, (Table I).

TABLE I

Number of intermetallic compounds that are present in binary systems containing noble metals in which room temperature compound formation takes place.

|    | In | Sn | Pb |
|----|----|----|----|
| Cu | 3  | 2  | 0  |
| Ag | 3  | 2  | 0  |
| Au | 4  | 4  | 2  |

TABLE II

Number of intermetallic compounds that are present in binary systems other than those containing noble metals in which fast diffusion effects take place.

|    | Ti    | Zr | Gd[1] | U[2]  |
|----|-------|----|-------|-------|
| Fe | 2     | 4  | 4     | 2     |
| Co | 5     | 5  | 7     | 6     |
| Ni | 3     | 8  | 7     | 6     |
| Pd | 8(10) | 4  | 6     | 5(7)  |
| Pt | 4(6)  | 3  | 8     | 4     |

[1] A Gd matrix is taken as a prototype for lanthanide elements, as one of the two components of a binary combination.
[2] Uranium matrix is taken as a prototype for other actinide elements, as one of the two components of a binary combination.
[3] In parenthesis, the number of intermetallic compounds including those stable at elevated temperatures or not yet well established.

Fast diffusion effects are not restricted to the above-mentioned systems. Other notable and relevant systems are combinations of an early transition metal element from the Group III-B (Sc, Y or a lanthanide element, Th and U) or from Group IV-B, (Ti, Zr or Hf) with a late transition metal from Group VIII (Fe, Co, Ni, Pd or Pt). Fast diffusion of the small size late transition metal elements in the matrix of the early transition metal elements has been reported in the literature. In these latter systems, however, none of the constituent elements has a melting point even relatively close to room temperature. Thus, in spite of fast interdiffusion, some exposure to intermediate temperatures is necessary in order to achieve any significant intermetallic compound formation within a reasonable time frame.

The formation of intermetallic compounds in even a relatively simple system such as two juxtaposed thin films, is a complex process. It depends on a number of variables such as the relative thickness of the individual initial layers, the diffusion mechanisms and the diffusivities of the atomic species in the different layers being formed, the nucleation characteristics of the various compounds, to mention just a few of the relevant parameters. It is not surprising, therefore, that in spite of the relatively large number of completed studies, no clear picture emerges regarding the outcome of the interdiffusion process in a thin film couple.

The thin film configuration, even though allowing an increase in the relative amount of compound to be formed at the interface, does not lend itself to the formation of bulk intermetallic compounds. Bulk formation of intermetallic compounds may be of both theoretical as well as practical interest. Bulk formation at room temperature and ambient pressure is of interest if extraneous constraints preclude the use of conventional processing and production methods, i.e. casting from the melt or diffusion assisted formation at elevated temperatures.

Another important use for powder metallurgy is its use in amalgams and related alloys. Metallic dental restorative materials used in dental fillings, placed directly in tooth cavity preparations, can be classified broadly into two classes, direct gold fillings and dental amalgams (O'Brien, 1989; Phillips, 1991). Dental amalgams are metallic composites resulting from a reaction between mercury and various pre-alloyed silver-tin-copper alloys. The mixing of mercury, which is liquid at ambient temperature, with the alloy in powder form takes place immediately prior to insertion in the dental cavity. The mixture, compacted into the cavity with dental instruments, consolidates into a cohesive solid and hardens over a length of time. Dental amalgams are much harder than pure gold fillings, they display relatively high compressive strength but are brittle and possess low transverse-rupture strength.

Amalgams and related alloys have been incorporated into a variety of commercial applications and thus a number of processes for producing such amalgams are known. For example, U.S. Pat. No. 4,664,855 discloses a universally employed process that triturates elemental metals or intermetallic alloys, in the form of comminuted filings or atomized spherical powders, with the sintering agent mercury and compacts the resulting amalgam into a uniform, consolidated metallic composite. The process may be considered a combination of liquid phase and reactive metal sintering. The finely comminuted metallic or intermetallic powders react with the Hg and when pressure is applied to the reaction product, form a compact, high density mass. U.S. Pat. No. 3,933,961 discloses a process for preparing a pre-weighed alloy tablet of uniform weight that is then triturated with a weighed quantity of Hg to form a traditional amalgam alloy.

The mercury content of dental amalgams has been a recurring source of concern because of the health and environmental hazards associated with its presence. Many aspects involved in the use of dental amalgams such as the various hazards, the possible substitute materials, their advantages and drawbacks, the economical considerations that are involved have been reviewed and discussed extensively in various publications as for example: Effects and Side-effects of Dental Restorative Materials", *Adv. in Dental Res.* 6:, September 1992; JADA Vol. 122, August 1991, papers p.54–61, p.63–65, p.67–71, p.73–77; JADA Vol. 125. April 1994, papers p. 381–387, p. 392–399).

Gold, either in the form of foils, powder or pellets can be used instead of mercury containing dental amalgams in direct filling. Prior to its condensation, pure gold, in all its forms, has to undergo a degassing procedure to desorb any adsorbed layers that might impede or prevent consolidation into a cohesive solid. Degassing is achieved by exposing the filling material to elevated temperature just before its insertion in the dental cavity. Clean gold surfaces and other noble metal surfaces, devoid of adsorbed layers, cold-weld under moderate pressure to form cohesive solids. Pure gold fillings are malleable and ductile and display high values of transverse rupture strength but low values of hardness and compressive strength.

SUMMARY OF THE INVENTION

One of the objectives of the present disclosure is to present a novel approach to low temperature compound formation in large quantities, using a method which takes advantage of the interdiffusion processes occurring at relatively low temperatures and ambient pressure.

In one aspect, this invention pertains to a metallic composite restorative material formed from a mixture of elemental metals, alloys and/or intermetallic compounds that have been given an appropriate surface treatment. The invention further pertains to a process for preparing the metallic composite by compacting the surface treated mixture of elemental metal powders, without adding a liquid metallic agent, such as mercury, to form a solid, cohesive metallic composite body, in situ. Compaction can be performed at ambient temperature, below the melting points of the surface treated powders present in the mixture, under pressure sufficient to form a uniform metallic composite.

Although not wishing to be bound by any one theory, the present inventors believe that the invention rests on several physical principles and specific findings that can be briefly described as follows:

i) Cold-welding takes place across appropriately treated metal surfaces, from which oxide or adsorbed gas layers have been removed. The present invention comprises treating the metal surfaces by immersion in reducing agent such as a mild or dilute acid to efficiently surface clean a noble metal (e.g. silver). Acid assisted consolidation of silver particles takes place at room temperature under moderate pressure to yield cohesive solids. As an extension of this finding, the present inventors have found that intermetallic compound particles or metal particles other than a noble metal, when coated with an external noble metal, or more noble metal layer readily undergo acid-assisted consolidation.

Noble metals are metals, as for example, silver, gold, platinum and palladium, which do not readily oxidize in air. Thus, more noble metals are those metals which have a more positive Standard Reduction Potential (SRP) in the electrochemical series (Handbook of Chemistry and Physics, page D-155, 61st Ed., 1980–81).

(ii) Metallic composite materials can be prepared from powder mixtures that include a soft ductile component, preferably a noble metal, e.g. silver, and hard intermetallic compound components that have been coated with a noble metal such as for example silver. Acid-assisted consolidation of such mixtures yields composites whose mechanical properties depend on the ratio of the soft to hard component.

(iii) Bulk quantities of intermetallic compounds can be prepared at ambient temperature if the interface area between the two metal components that interdiffuse is sufficiently large. By taking advantage of a coating process, as for example, but not limited to, electrolytic deposition from a fluidized bed, physical deposition processes and an immersion deposition process whereby a more noble metal, e.g. silver, deposits from a solution in which a less noble metal, e.g. tin, has been immersed in the form of solid powder particles. A huge interface area between the more noble and less noble component equal to the surface area of the less noble (e.g. tin) particles is thereby produced. In such a system, bulk quantities or even complete transformation into intermetallic compound can be obtained. Such a material, when mixed with or containing a sufficient amount of a noble metal, will readily undergo acid assisted consolidation and yield a cohesive solid whose mechanical properties such as transverse rupture strength, compressive strength and hardness can be adjusted by varying the relative amount of the various components.

The metallic composites prepared by making use of the above are useful as dental restorative materials, specifically as mercury-free alternatives to dental amalgams.

In summary, this invention pertains to 1) the synthesis of bulk quantities of intermetallic compounds ($A_mB_n$), 2) the synthesis of finely dispersed two-phase alloys and 3) synthesis of metallic matrix composites (MMC) at temperatures significantly lower than the melting temperature of the constituent elements, 4) application of immersion coated metallic powders to synthesize composites, 5) application of fast interdiffusion couples to promote compound formation making use of acid assisted consolidation techniques.

BRIEF DESCRIPTION OF THE DRAWINGS

FIG. 10 are diffraction patterns of a consolidated Ag-coated atomized Ag—Sn alloy powder sample, similar to that described in Example 6, but coated by a different chemistry.

DETAILED DESCRIPTION OF PREFERRED EMBODIMENTS

Figure 1:
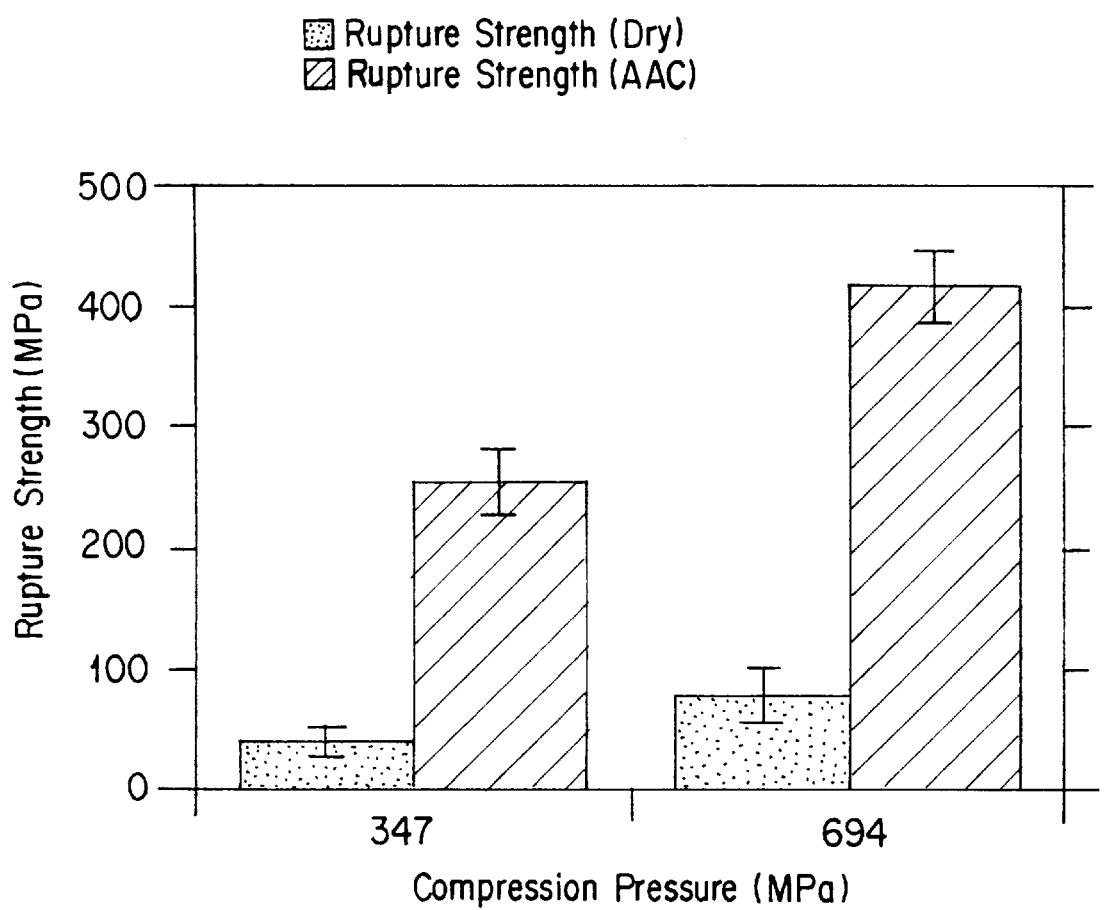
FIG. 1 shows values of transverse rupture strength of consolidated silver powders. The figure shows the effect of the compression pressure and the significant increase in rupture strength achieved by acid-assisted consolidation (AAC).

In one aspect the present invention pertains to a process for forming metallic restorative metallic composites or alloys which circumvents the need for a metallic liquid sintering agent such as mercury, indium, or gallium or other low melting-point metallic alloys and relies on an alternative to the so-called amalgamation process or to the gold filling process.

This process relies on a combination of liquid acid assisted consolidation and fast diffusion effects that take place in some metals and their alloys.

Liquid acid assisted consolidation (AAC) enables cold-welding of loose powder particles, foils or sheets under moderate pressure at ambient temperature into a cohesive solid. The present inventors have found that such cold-welding, that takes place across particle surfaces that are in contact, can be made possible by appropriately surface treating the particles as an alternative to traditional high temperature exposure, commonly used to cold-weld gold surfaces. Specifically, in accordance with the present invention, noble metals (or more noble metals), e.g., silver, gold, palladium and copper, cold-weld after having undergone suitable surface treatment by immersing the metal provided in particles, foils or sheets in a reducing media based on water, alcohol or oil that has the property of removing surface oxides. Preferred reducing media include mild or dilute acids, in order to remove the surface oxide layers. Suitable acids for use in the surface treatment according to this invention include, but are not limited to organic acids such as for example acetic acid or inorganic acids, as for example, fluoroboric acid, sulfuric acid, hydrofluoric acid, hydrochloric acid, sodium asorbate, potassium asorbate, citric acid, adipic acid, ascorbic acid, sulfamic acid with or without ammonium bifluoride and nitric acid. Suitable concentration for the acid for use in the invention are from about 1% to about 30%. The nature and concentration of the reducing media depends on the nature of the application. For example, in dental applications, fluoroboric acid is preferred in concentrations ranging from about 2 to about 10% by volume, with about 2.5% by volume being most preferred.

The surface treatment, essentially an electrochemical treatment, which can be carried out at about ambient temperature, comprises thorough cleaning of particulate, metal or pre-alloyed intermetallic compound, and removal of the surface oxide layers by immersion in the acid solution.

The present invention should not be construed to be limited to reducing the surface oxides solely by reducing media. Oxides on particles can also be, for example, electrolytically reduced even in oxidizing solutions by applying a negative potential. In particular, solutions containing sulfate can be used to reduce the oxide on iron by applying a negative potential even though the oxide will reform once the potential (voltage) is removed.

The present invention further pertains to a process based on the aforementioned embodiment wherein non-noble metals, as for example, but not limited to, Ga, In, Ir, La, Re, Rh, Ru, Sn, Ti, Y, Zn, Nb, Mo, Ta, Sc, Hf, Th, Ce, Pr, Nd, Sm, Gd, TB, Gy, Ho, Er, Tm, Yb or Lu; or intermetallic compound particles are cold-welded by providing them with an external oxide-replacing metal coating of a more noble metal, as for example such as Ag, Au, Pd, Fe, Ni, Cu, Co or Pt. The process comprises immersing the non-noble metals or intermetallic compound particles in a solution containing an electrolyte. The electrolyte is for example, but not limited to, at least one sulfamate, iodide, cyanate, nitrate, pyrophosphate, fluoroborate or sulfide salt of the oxide-replacing (more noble) metal. An electrolytic or coating process is conducted or replacement reactions are allowed to form the coating and subsequently separating by filtration, centrifuge, evaporation or other suitable means, the coated powder from the electrolyte solution. The coated powder is then cleaned, rinsed and immersed in a liquid acid solution and consolidated into a cohesive solid. The particles are coated in order to ensure that each particle has an external surface from which any oxide layer can be removed efficiently so that it readily undergoes cold-welding under moderate pressure. Contrary to known "cold-welding" of gold fillings discussed in the background above, no exposure to high temperature is required prior to consolidation of the coated particles.

Other methods for removing oxides from the metal surfaces and preventing further oxide formation, other than the electrochemical method described above, may also be used. For example, gas plasmas with inert and reducing atmospheres, such as the forming gas (5% hydrogen and 95% nitrogen), also remove surface oxides from metals. Similarly, vapor deposition, sputtering or mechanical plating will coat the powder particles with protective layers of Ag, Au or a related alloy which has non-tenacious oxides.

Figure 2:
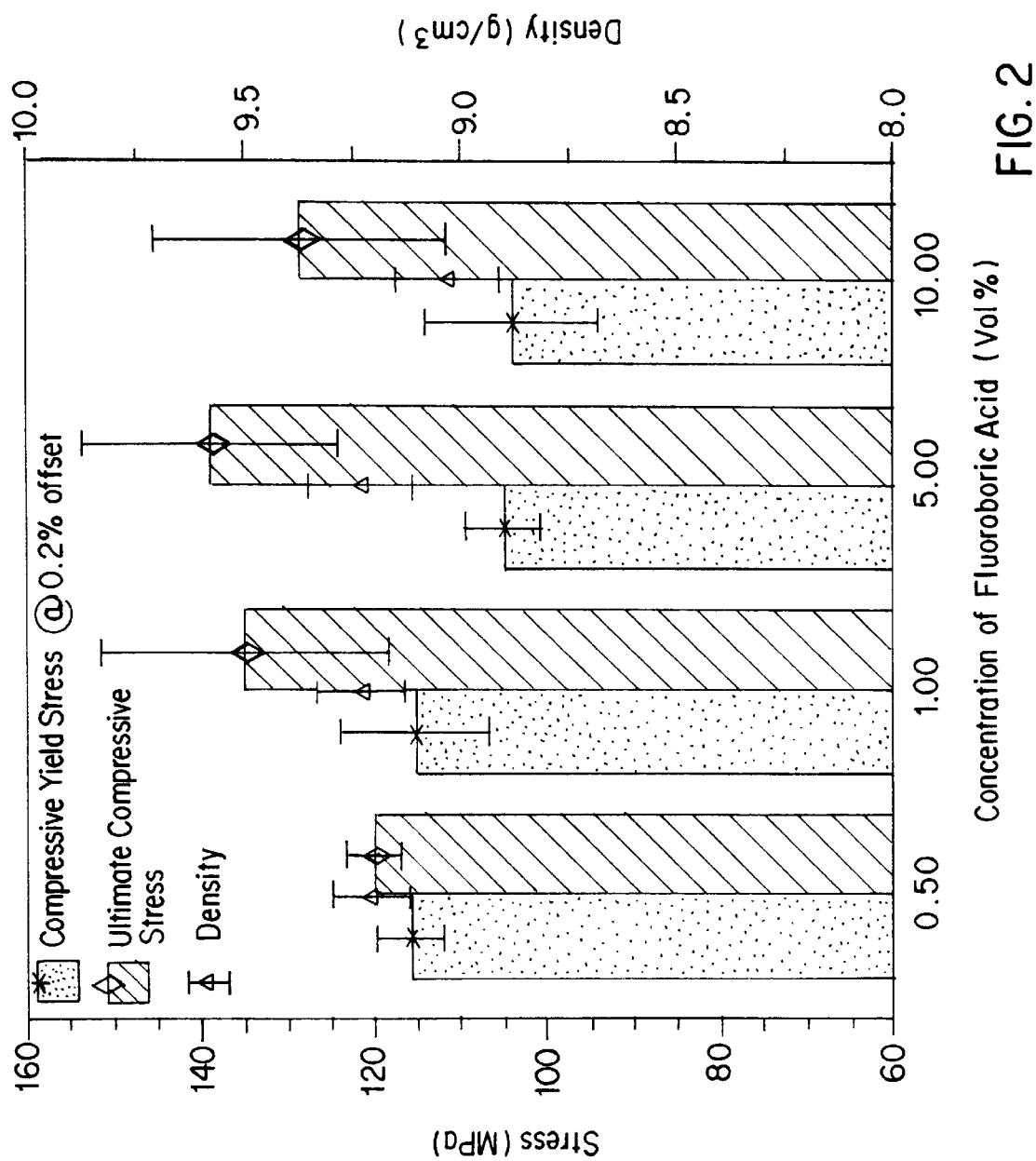
FIG. 2 shows the effect of the acid concentration on the density and compressive strength of silver powders that have undergone acid-assisted consolidation by impact.

As a direct filling alloy for dental applications the powders, foils and sheets may be subjected to a cathodic and/or anodic treatment which is followed by an acid treatment. The thus treated wet powders, foils and sheets are consolidated into a net shape. The cathodic and/or anodic treatment may be in combination with a rinsing step or may be eliminated in certain circumstances. Depending on the particular elemental, metallic, intermetallic or alloy used, there may be an optimal concentration of the acid. Preliminary results are shown in FIG. 2, wherein the density and the strength are measured in compression as a function of the acid concentration.

The liquid present between the suitably coated powder particles seeps out from between the particles (foils or sheets) during the acid assisted consolidation. The liquid provides a very important secondary benefit in that very small powder particles are constrained under the surface of the liquid so that they can be handled more safely. In instances where the particles are used as in situ dental restorations, the patient will not inhale them, Another benefit of the liquid is lubrication of the compressed particles.

The "non-amalgamation" process described herein relies on fast-diffusion effects that take place in some metallic systems. Fast-diffusion as discussed above, is attributed to the ability of some diffusing species to penetrate interstitially into a host matrix. Diffusion takes place via an interstitial mechanism instead of the usual vacancy mechanism characteristic of diffusion in most metal systems. Interstitial diffusion is usually much faster than diffusion governed by the metal-vacancy mechanism. The fast-diffusing species are small-size, low-valence constituents (e.g., Ag) which diffuse rapidly within the host matrix of a large-size, usually high valence component (e.g. Sn). Similar behavior has been observed for mono-valent metals (e.g., Cu, Ag and Au) and some transition metals (e.g., Fe, Co, Ni and Pd) as diffusing species in Group IV-B metals (Sn, Pb), Group III-B metals (In) and some early transition metals (e.g., Y, La, Ti and Zr) as metal matrices.

Fast diffusion effects are relevant to the "non-amalgamation" insofar that they promote intermetallic compound formation at ambient temperature. When the two components of such a fast-diffusing system are put in physical contact, interdiffusion occurs. For example, the intermetallic compounds $Ag_3Sn$ and $Ag_4Sn$ may be prepared by interdiffusion of silver and tin. Silver will diffuse rapidly into tin and also tin into silver (via grain-boundaries), until the respective solubility levels, (of silver in tin and tin in silver) are reached. At the solubility limit, the intermetallic compounds $Ag_3Sn$ and $Ag_4Sn$ form. The amount of intermetallic compound that forms at the interface of mixed powders depends on the contact area between the tin and silver particles. The amount of intermetallic compound formed near that interface at about body temperature, preferably about 37° C., is limited. Typically, the amount of intermetallic formed does not exceed the layer width of the interface region of about 0.5 to 1 $\mu$m.

AS mentioned above, mixing elemental silver and tin powders will lead to the formation of a certain amount of Ag—Sn intermetallic compounds. In order to increase the volume fraction of the $Ag_3Sn$ and $Ag_4Sn$ compound in the final product, comminuted amounts of $Ag_4Sn$ and/or $Ag_3Sn$ may be preferably added to an initial mixture of silver and possibly tin. The resulting initial mixture preferably consists of a certain weight fraction of the intermetallic compound with elemental silver, and/or silver based alloys. Elemental tin may also be added to the initial mixture. The relative fraction of the powdered, pre-alloyed intermetallic $Ag_3Sn$ and /or $Ag_3Sn$ in the mixture may preferably range from 0 to 70 percent.

The formation at ambient temperature of intermetallic compounds by direct interdiffusion of silver and tin is illustrated in Examples 2 to 7. Fast interdiffusion and resulting intermetallic compound formation are not restricted, as mentioned, to the Ag—Sn system. Other possible combinations of fast interdiffusing metals will give rise to ambient temperature compound formation, as shown in Examples 8 and 9.

The properties of the consolidated material are determined by the properties of the starting materials incorporated into the mixture, by the relative amount of each component, by the surface treatment applied and by the details of the consolidation procedure that was used. Thus, increasing values of pressure applied for consolidation increase the density, compressive strength and rupture strength of the final product. The condensability, namely its propensity to transform from a loose powder or slurry into a cohesive solid, and the transverse rupture strength are increased by increasing the unalloyed metal, e.g. silver, content of the mixture. Increased levels of hardness and compressive strength can be attained by incorporating into the mixture fractions of pre-alloyed intermetallic compounds which, in general, are much harder than the unalloyed metals. These compound particles can be spherical or lathe cut pre-alloyed silver-tin intermetallic compounds, for example, with various additions of other alloying elements. Pre-alloyed intermetallic compounds containing other components can also be considered. Moreover, non-metallic hard compounds such as oxide, carbide or nitride particles in the form of high-strength structural whisker, particulate or fiber additives can also be incorporated in the mixture. Such additives may include, but are not limited to, alumina powder, silicon carbide powder, graphite, diamond, sapphire, or the like. Other whisker, fiber or particle additives are within the scope of the invention. In addition, or instead of the pre-alloyed intermetallic compounds or other compounds, a hard intermetallic compound fraction can be formed in-situ within the consolidated mixture. In-situ formation implies compound formation of bulk quantities of intermetallic compounds, as previously described, after the mixing of the powder components has taken place.

Metal combinations which give rise to intermetallic compound formation include, but are not limited to, members of the group consisting of Au, Ag, Fe, Pt, Pd, Ni, Co and Cu as a first component in combination with a member selected from the group consisting of Ga, In, Ir, La, Re, Rh, Ru, Sn, Ti, Y, Zn, Nb, Mo, Ta, Sc, Hf, Ce, Pr, Nd, Sm, Gd, Tb, Dy, Ho, Er, Tm, Tb, Lu, U, Th and W. A preferred metal combination that gives rise to intermetallic compound formation contains a first elemental metal, Sn, and a second elemental metal, Ag. A preferred Ag:Sn ratio of the two metals is from 4:1 to about 3:2. More preferably, the Ag:Sn ratio is from 4:1 to 3:1.

In order to ensure adequate condensation of a powder mixture that includes pre-alloyed intermetallic compound or other hard particles into a cohesive solid, it is preferred that these particles be provided with an external coating that is prone to cold-welding. Preferably this coating should be a more noble or noble metal, e.g., silver coating. As previously mentioned silver surfaces readily undergo acid assisted consolidation.

The external surface coating can be provided by any technique for surface coating of powder particles. These include coatings from a gaseous or from a liquid phase. Gaseous coatings include but are not limited to fluidized bed, vacuum evaporation, sputtering, plasma assisted and other techniques. Coatings from a liquid phase include but are not limited to electrolytic, as for example electrolytic coating from a fluidized bed onto particle or fibers; immersion or substitution deposition. One example of a fluidized bed coating technique is described in a copending application of some of the present inventors entitled "Electrochemical Fluidized Bed Coating of Powders", hereby incorporated herein in its entirety by reference, filed concurrently herewith and having Attorney Docket No. 53917.

Figure 12:
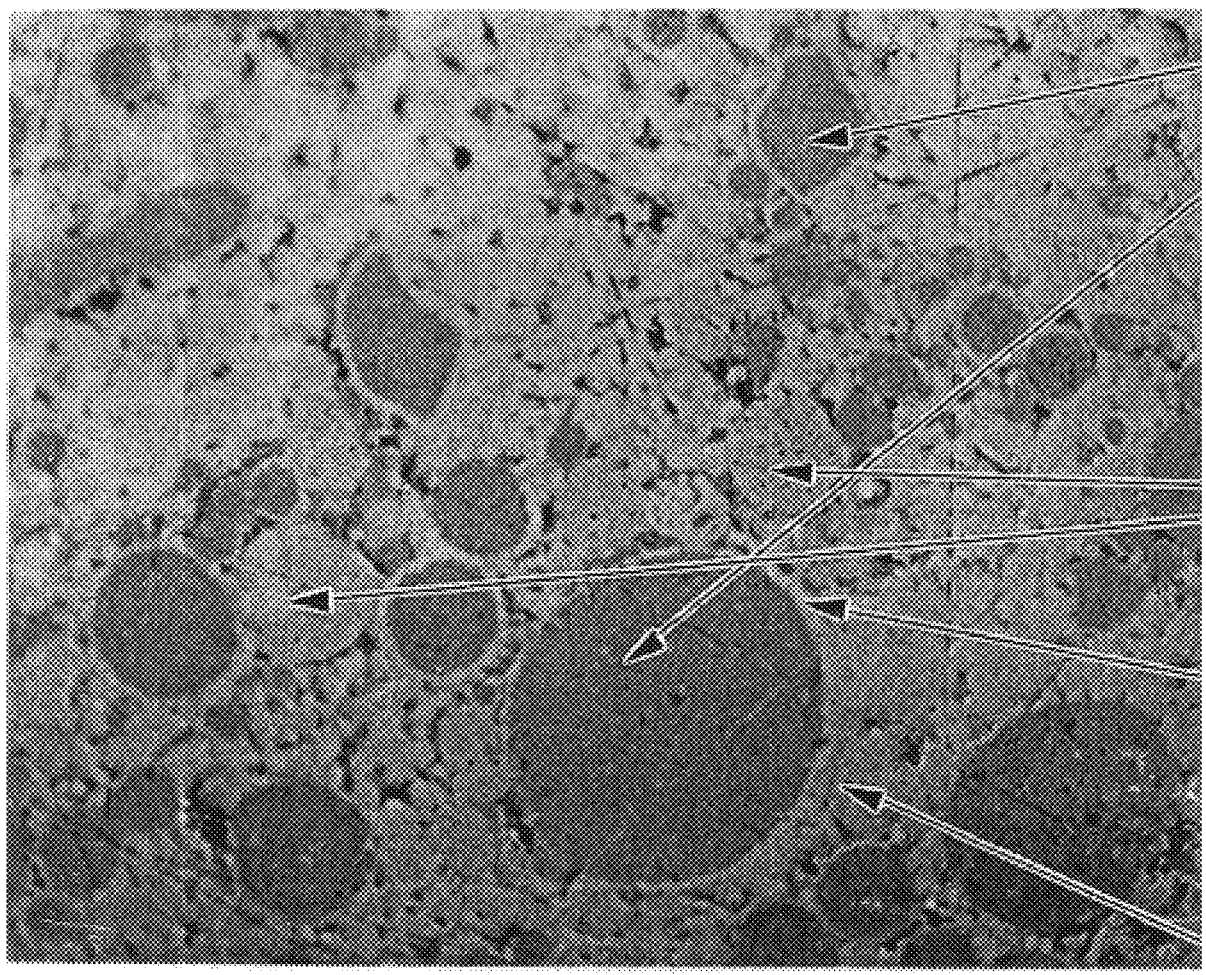
FIG. 12 is a micrograph of a consolidated, atomized composite dental alloy, consisting of Ag-coated, atomized $Ag_3Sn$ particles, atomized Cu—Ag alloy particles embedded in a matrix consisting of free Ag particles (Example 7).

For example, FIG. 12 represents a silver-coated $Ag_3Sn$ powder mixed with elemental Ag, Sn and atomized Cu—Ag alloy particles and then consolidated. The $Ag_3Sn$ particles have a thin Ag coating. The silver-coated $Ag_3Sn$ particles bond well to the free Ag particles which make up most of the Ag matrix. The atomized Cu—Ag particles provide increased hardness to the material.

After the elemental metallic, alloy, intermetallic or other hard constituent powder particles are coated with a more noble metal, as for example, silver, gold, or copper, a consolidated composite solid body such as a dental restoration may be formed, in situ (e.g., in a dental cavity or mold for a commercial press), by compacting the wet surface treated mixture of the oxide-free and coated powders, without adding any metallic liquid sintering agent. Examples of compacting include, but are not limited to, die press and sinter, roll bonding, extrusion, "hipping" (hot isostatic pressing), "hot pressing or cold pressing", or compacting with normal or modified dental instruments in situ in a patient's mouth.

Immersion or substitution deposition of silver or gold is an extremely useful method, in the context of the present invention, in order to provide a very finely dispersed deposit of silver or gold. According to this technique, a metallic powder, consisting either of elemental metal, alloy or intermetallic compound particles, is immersed in a aqueous solution of a more noble metal. The less noble metal constituents of the immersed solid powder undergo partial oxidative dissolution in the solution, concurrently with the reduction and deposition of the more noble metal from the solution. This method allows the creation of a large interface area between the residual, partly dissolved solid particles and the more noble, metallic deposit from the solution. The advantages of this method of deposition of the noble metals silver or gold are twofold. Firstly, a pure silver or gold deposit is provided uniformly through the mixture. Such a deposit will provide the required interface material that readily cold-welds by acid assisted consolidation. Secondly, if the initial solid particles, after their partial oxidative dissolution, still contain metallic elements which are defined as appropriate host metal for fast diffusion, e.g., Sn, the conditions for the formation of intermetallic compounds by fast interdiffusion are met. Moreover, this method provides a mixture of powders, i.e. the initial solid powder e.g., Sn-containing particles coated with the fine Ag deposit, that displays a large Sn—Ag interface area. Maximum interface area will, of course, be achieved by having each individual tin (or tin-containing compound) particle coated by a silver layer. At each tin-silver interface, interdiffusion takes place leading to the formation of additional $Ag_4Sn$ compound until the compound layer thickness acts as a barrier to further interdiffusion. A high compound content of the product, prepared according to this approach, is shown in Examples 3, 5, 6 and 7. In all these cases, the powder particles were provided with a silver environment by having the silver deposit from the solution. In Example 3, the particles are pure Sn particles, in Examples 5, 6 and 7 they are silver-tin compound particles with about 18 wt. % free tin content. The diffraction patterns taken after different time intervals after the samples had been consolidated show an appreciable increase of the compound $Ag_4Sn+Ag_3Sn$ fraction in the final sample. Even in Example 4, in which a nominally stoichiometric compound was silver coated, an increase of the compound content was observed after the sample had been kept at 37° C. for 64 h. In this case, in spite of the nominal stoichiometric composition, the free Sn (which originated from the fast cooling of the atomized powder) reacted with silver and yielded some additional $Ag_4Sn+Ag_3Sn$ compound fraction.

Compound formation by this method is not limited to powders in which a large Ag—Sn interface is created. Example 8 illustrates compound formation in the Ag—In system, Example 9 illustrates compound formation in Au—Sn systems, Example 12 illustrates compound formation in Cu—Sn systems, respectively.

An in situ dental restoration, as for example dental fillings, is a preferred application of the compacted alloy thus formed. In one embodiment, commercially available amalgam powder packages (without the Hg component) may be surface treated according to the process of the invention, mixed with appropriate other powders and subsequently compacted to form a consolidated alloy. These commercially available powders may typically consist of combinations of intermetallics which may contain copper and/or zinc (these intermetallics typically approximate the $Ag_3Sn$ compound). In another embodiment of the invention, Ag and pre-alloyed intermetallic compounds at or close to the $Ag_3Sn$ composition coated with silver or gold are compacted at body temperature. In still another embodiment of the invention, elemental tin powder, silver-coated, is mixed with silver and/or silver-copper alloy powder particles and compacted at body temperature.

A preferred coated powder used in dental applications is $Ag_3Sn$ and/or $Ag_4Sn$ and a preferred elemental powder is Ag, with a preferred overall Ag:Sn atomic ratio ranging from 3:1 to about 8:1.

Pre-alloyed intermetallics, subsequently combined with elemental silver and/or tin particles, may consist of a compound having a weight ratio of Ag:Sn ranging from about 5:1 to about 3:1. In these compounds an excess tin may be locally present. This excess can be compensated for by increasing a weight ratio of the elemental silver to intermetallic compound.

The in situ formation of the alloy preferably occurs at a temperature below the melting point of the coated powders and under an applied pressure. Exemplary ranges of temperature and pressures under which the alloys may be formed include, but are not limited to, from 20° C. to about 100° C., and from 20 MPa to about 400 MPa, respectively. A preferred temperature for the consolidation of the composite for dental restorative purposes is about body temperature. A preferred pressure is about 200 MPa or approximately the pressure exerted by ordinary dental tools.

It is preferred to optimize the space filling ability of the powder mixture. It is also preferred to increase the contact area between the powder particles. Intermetallic compounds of the invention may have exemplary equiaxial particle sizes ranging from 0.5 μm to about 100 μm. Preferably, the particle sizes of the powders range from about 0.5 μm to about 40 μm. Space-filling is improved by having multimodal particle size distributions. Preferably, the mixture should consist of particles in the 30 to 40 μm size range admixed with particles in the 2 to 10 μm size range.

In yet another embodiment of the invention, the process can be applied to systems in which neither solid solutions nor intermetallic compounds are formed. An alloy consisting of two such metals will display a mixture of two phases, associated with the two components. The homogeneity of such a mixture will depend on the initial particle size and the conditions under which mixing was carried out. In many instances the properties of such alloys follow the rule of mixtures law and scale with the respective concentration of the components. An immersion coating process can be taken advantage of in order to ensure a homogeneous distribution of the two components at a scale which is determined by the particle size of the component that is added in the form of powder to the solution. Thus, physical and electronic properties can be engineered as for example, thermal diffusivity, thermal conductivity, the coefficient of thermal expansion, magnetic properties and electronic properties can be custom-tailored to specific situations by using the process according to the present invention. Engineering properties of coated particles by controlling the relative volume fractions of the particulate material and the coating material is described in a copending patent application of one of the present inventors (U.S. patent application Ser. No. 08/102,532, filed Aug. 4, 1993, now U.S. Pat. Nos. 5,453,293, 5,601,924 and 5,614,320, issued Sep. 26, 1995, Feb. 11, 1997 and Mar. 25, 1997, respectively which is a continuation of Ser. No. 07/731,809 filed Jul. 17, 1991 ABN), entitled "Methods of Manufacturing Particles and Articles Having Engineered Properties and Applying Coatings Having Engineered Properties to Articles", hereby incorporated herein in its entirety by reference.

The previously described immersion or substitution deposition of metals is used to form the uniform and fine distribution of the two components. The electrolyte containing the more noble component has to be able to dissolve the less noble component initially immersed as a solid and also to dissolve any protecting oxide layer present on its surface.

Such binary combinations display immiscibility of their components up to 1000° C. In these combinations, the less noble metal is one of the group that includes the metals Nb, Mo, Ta and W, while the more noble component is a metal that belongs to the group Cu, Ag and Au. Example 10, i.e. the Cu—W system, illustrates one of these combinations. Table III displays representative examples of combinations of binary systems which display immiscibility of their components (at at least 1000° C.) and which can be prepared according to this invention.

TABLE III

|    | Nb | Mo | Ta | W |
|----|----|----|----|---|
| Cu | ✓  | ✓  | ✓  | ✓ |
| Ag | ✓  | ✓  | ✓  | ✓ |
| Au | ✓  | ✓  | ✓  | ✓ |

The rapid formation of bulk quantities of intermetallic compounds at relatively low temperatures relies on the generation of a large interface area between the powder particles (constituent A) and the immersion deposited coating (constituent B). Compound formation at ambient temperature also relies on fast interdiffusion effects that occur in several binary combinations. By adjusting the free parameters of the system, i.e. amount of powder, concentration of the metal ions in the solution, pH of the solution, temperature and duration of the immersion coating process, the composition of the product material is pre-determined. The composition of compound-forming coated powders determines the structure, and hence the properties of the resulting compound. Pre-determining the composition of two-phase alloys or metal matrix composites, allows the custom-design of materials with desired properties or combination of properties. By compressing the coated powder in appropriate dies, or, alternatively, by the use of processes such as extrusion forming or injection molding, the product material, i.e., the intermetallic compounds, two-phase alloys or metal matrix composites can be formed into near-net shape parts.

Figure 16:
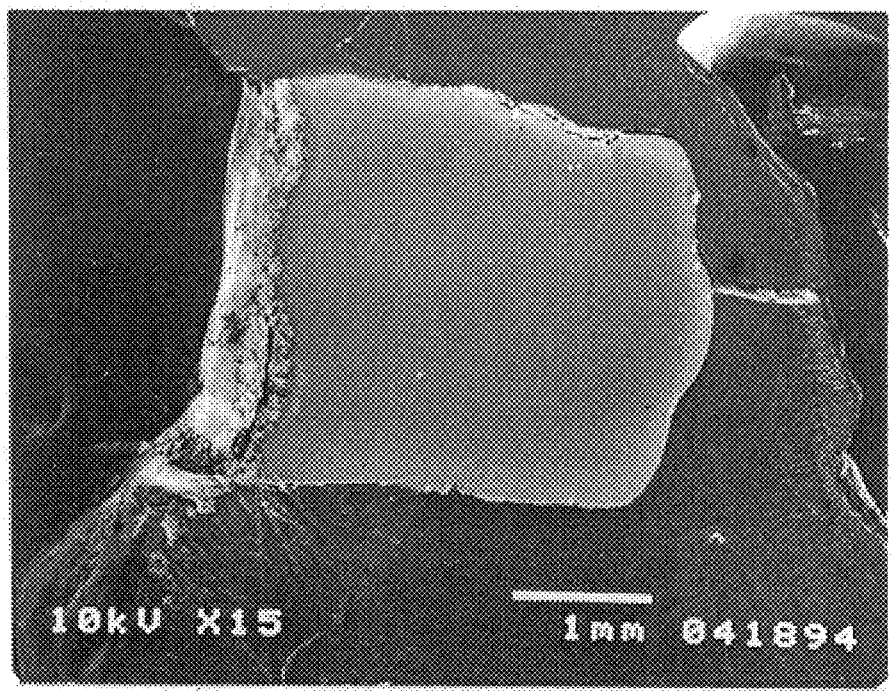
FIG. 16 is a low magnification scanning electron micrograph of a cross section of a tooth containing a filling consisting of a mixture of electrolytically silver-coated $Ag_4Sn$ that had been mixed with elemental silver and elemental tin particles and immersion coated with silver. This mixture was hand-consolidated with conventional dental instruments.
Figure 17:
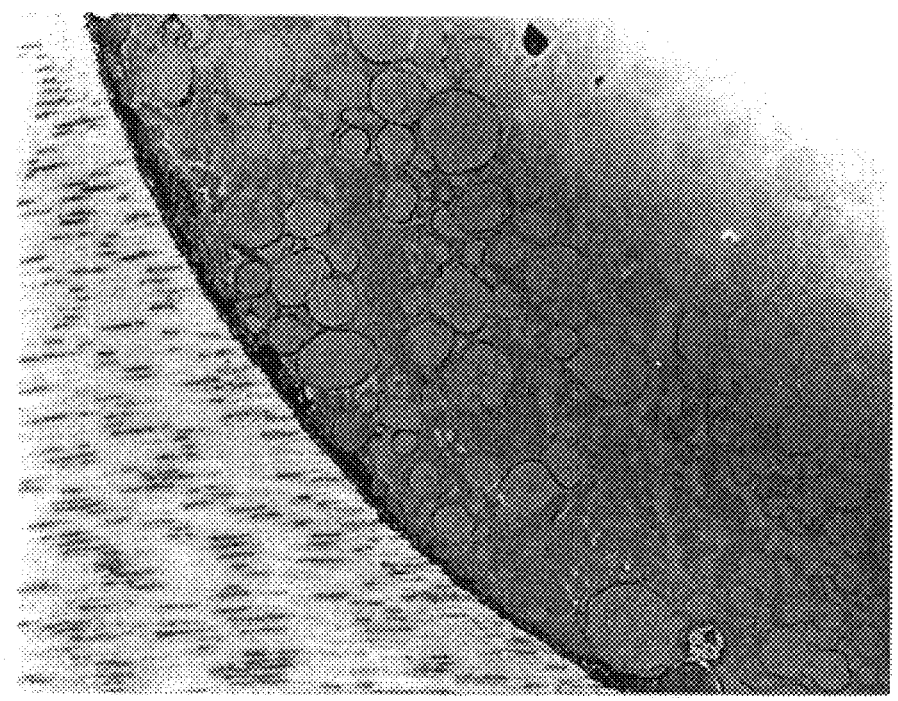
FIG. 17 is an optical micrograph of the dentin-filling interface of the filling shown in FIG. 16.

Examples of various methods of preparation of powder mixtures that can be transformed into bulk intermetallic compounds at near ambient temperature and under moderate pressure are described in the following non-limiting Examples 2 to 12. Most examples (2 to 7) are concerned with the Ag—Sn system which is considered as the paradigm system for applications as dental restorative materials. An actual typodont filled with a restorative material prepared according to the methods described hereby is shown in FIG. 16. A higher magnification optical micrograph of the interface area between the dental filling material and tooth structure and illustrating the good bonding is shown in FIG. 17. Finally a photograph of an extracted tooth with a mercury-free filling prepared according to the above-described methods is shown in FIG. 18.

Examples 8, 9, 11 and 12 illustrate a more general aspect of the invention, wherein the inventive processes are applied to form bulk intermetallic compounds in additional systems. Finally, Example 10 illustrates the potential of applying some of the processes to non-compound forming systems in order to achieve homogeneous fine-scale mixtures of different phases.

EXAMPLES

In the Examples which follow wherein a 10% (20%) fluoroboric acid solution is used, it is prepared by mixing 100 ml (200 ml) of concentrated (48%) $HBF_4$ (ALFA cat. #11484) with 900 (800) ml of distilled $H_2O$.

Example 1

In this Example the fraction of hard component in the resultant compact is reduced to zero.

Silver powder is stirred for 5 min in a 10% $HBF_4$ solution and consolidated in near-net-shape molds for density, compressive and transverse rupture strength determination. For reference purposes, dry silver powder is also consolidated and its transverse rupture strength determined. The results are shown in FIG. 1 and illustrate significant increase of transverse rupture strength resulting from the surface treatment of the silver powder. This surface treatment increases the compressive and transverse rupture strength of both spherical and dendritic silver particulates. The density and the compressive strength of the consolidated silver as a function of the concentration used in the acid-assisted consolidation process is shown in FIG. 2.

Example 2

Figure 3:
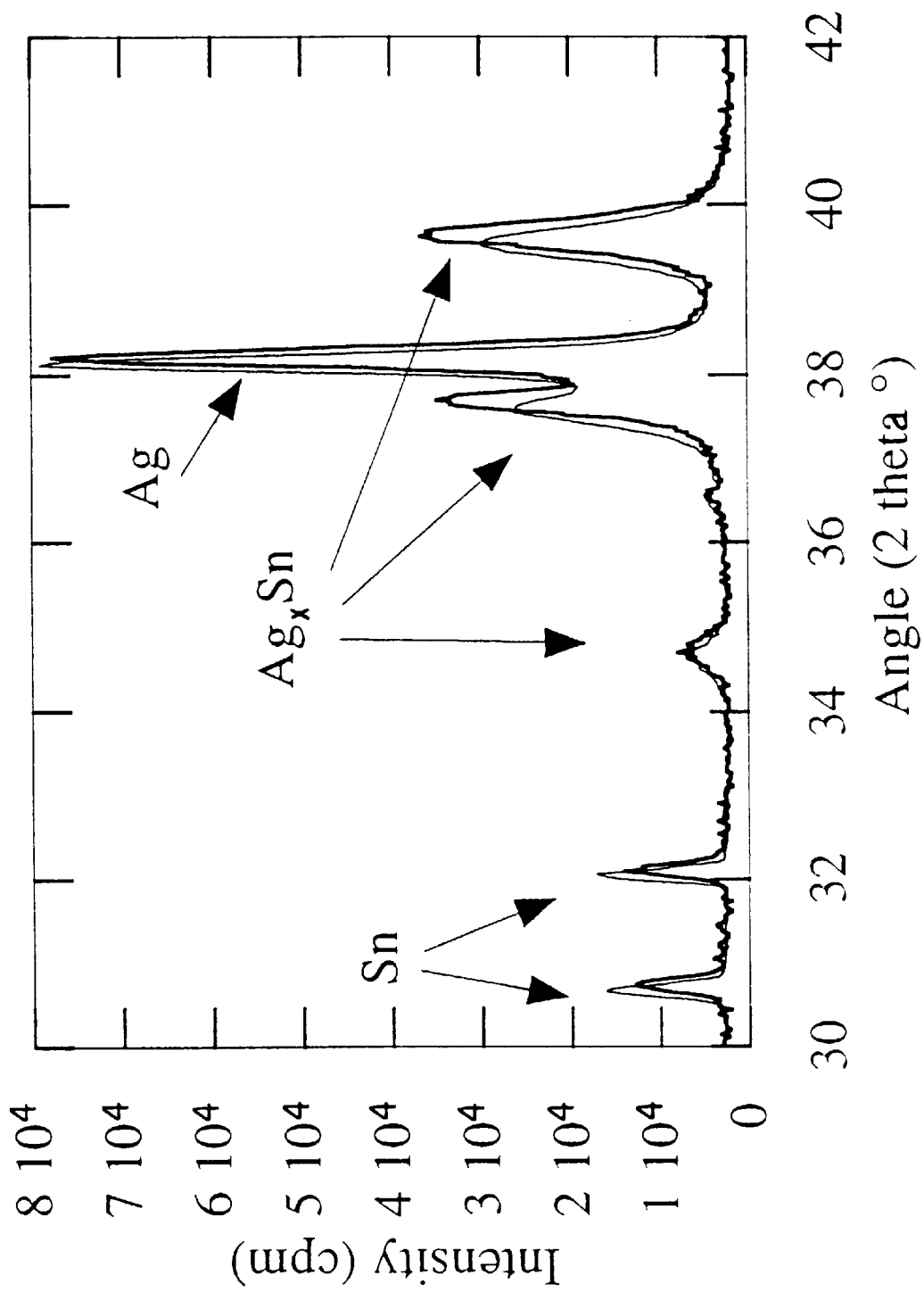
FIG. 3 shows two superimposed x-ray diffraction spectra of a sample prepared according to the procedure described in Example 2. These spectra illustrate the compound formation at ambient temperature.

An amount of 1 g of −325 mesh atomized $Ag_3Sn$ compound, 0.9 g of Ag powder, 4–7 µm size, 99.9% (ALFA Cat.#11402) and 0.8 g Ag powder, 1–3 µm, 99.9% (ALFA Cat.#11405) and 0.5 g Sn metal powder 99.8% pure, (−325 mesh, 12.5 µm average size from CERAC™, Cat. #T-1120) are stirred in 500 ml 10% $HBF_{4+}$ 0.2% $(NaPO_3)_{6,}$ (Fisher, cat. #S-333) for 5 min. The liquid is decanted and the solid residue is compressed into a pellet at 440 MPa. X-ray diffraction spectra (FIG. 3, thin line) taken immediately after consolidation reveal the presence of the three components in the mixture, namely elemental Ag, Sn and the compound $Ag_3$ Sn. A second x-ray diffraction pattern (FIG. 3, thick line) obtained after a 19 h stay at 37° C., shows an increase of the $Ag_3Sn$ peaks and a decrease of the Sn peaks. These spectra prove formation of the intermetallic compound $Ag_3Sn$ at near room temperature.

Example 3

Figure 4A:
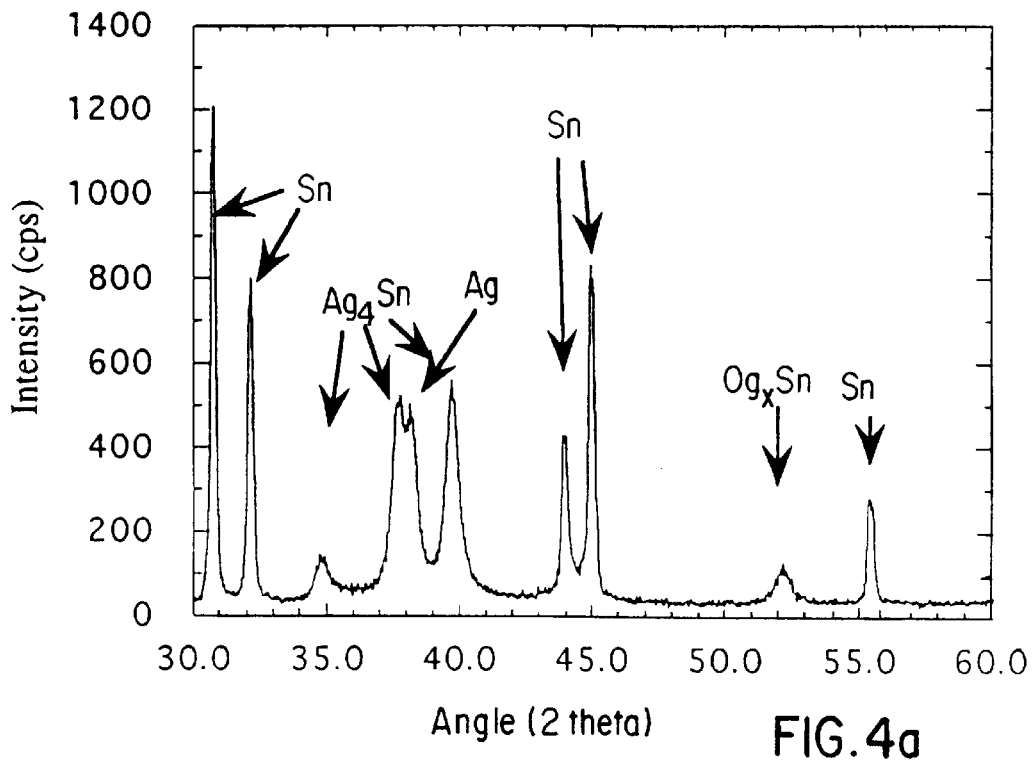
FIG. 4 are x-ray diffraction spectra of a consolidated sample of Ag-coated Sn powder (Example 3) taken at different times after consolidation. Spectrum 4a was started 30 min after consolidation, spectrum 4b was taken 8 days later.
Figure 4B:
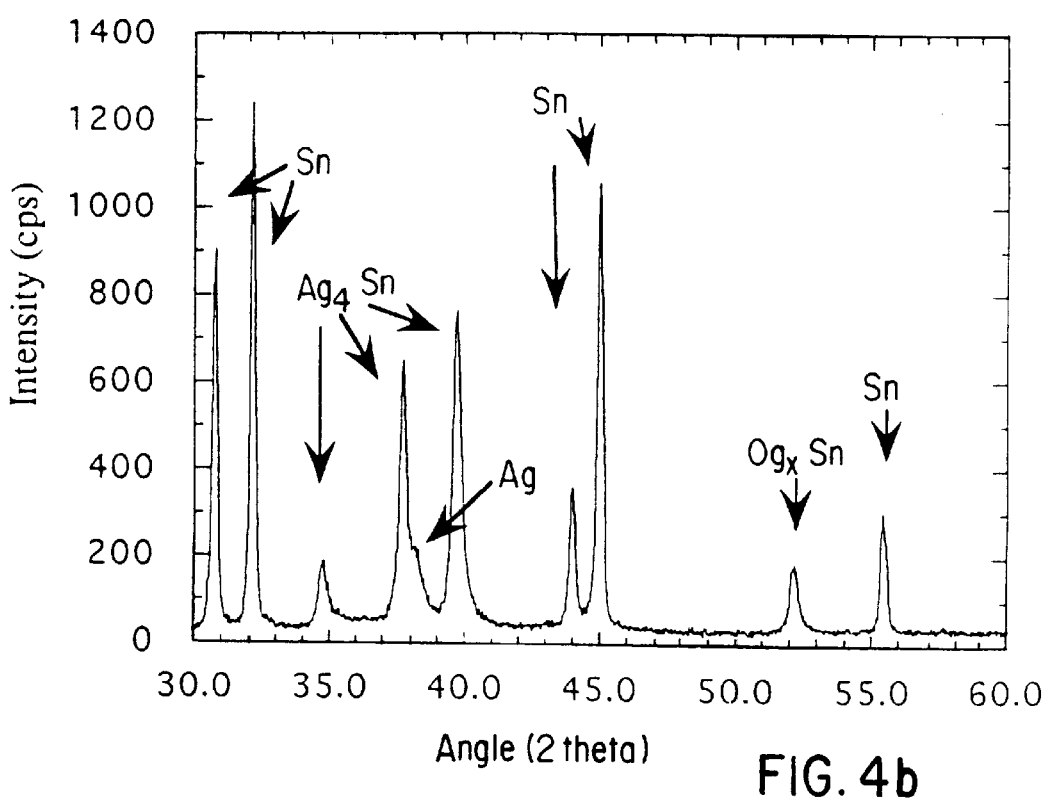

A solution of 12.10 g/L $AgBF_4$ (Aldrich, Cat. No. 20,836-1) in 20% $HBF_4$ is prepared. 8.02 grams of Sn metal powder, 99.8% pure, (−325 mesh, 12.5 μm average size from CERAC™, Cat. #T-1120), is added to the solution and stirred for 50 min. The powder is allowed to settle, the liquid removed and the remaining slurry is rinsed in a 10% $HBF_4$ solution. The powder is allowed to settle again and the slurry removed. A pellet is pressed from the slurry, at 1,178 MPa in a steel mold. X-ray diffraction analysis of this pellet started within 30 min of its preparation. The diffraction pattern that is obtained is shown in FIG. 4a. Analysis of the diffraction pattern reveals the presence of elemental Sn, elemental Ag and an appreciable fraction, approximately 30%, of intermetallic compound (a mixture of $Ag_4Sn$ and $Ag_3Sn$). The diffraction lines of the compound are broadened as a result of: (1) a spread of composition, due to the width of the composition range corresponding to this compound (see Ag—Sn phase diagram); (2) its formation by means of solid state inter-diffusion between elemental Ag and elemental Sn. In addition, the diffraction lines of the compound $Ag_4Sn$ overlap partly those of the $Ag_3Sn$ compound, causing further line broadening. FIG. 4b shows the diffraction pattern of the same sample after it had been kept at 37° C. for 8 days. The intensity of some of the diffraction peaks of elemental Sn of type (hk1=0) decreased, while the diffraction lines of type (hk1≠0) increased, the intensity of all diffraction peaks due to elemental Ag decreased and those due to the intermetallic compounds $Ag_3Sn$ and $Ag_4Sn$ increased and narrowed. These results prove that the reaction between elemental Sn and elemental silver proceeded at 37° C. and that, in parallel, the texture of the elemental Sn underwent some changes. Noteworthy is also the narrowing of the diffraction lines of the intermetallic compound, reflecting its increased homogenization. Apparently, the thickness of the compound layer that had formed at the Sn—Ag interfaces in the course of the first 8 days following the sample preparation impedes further compound formation. Indeed close examination of FIG. 4b shows that some elemental tin and some elemental silver were still present in that sample after 30 days.

The rupture strength of one sample prepared from the powder/slurry, measured by means of the three point bending test, was 165±5 MPa.

Figure 5:
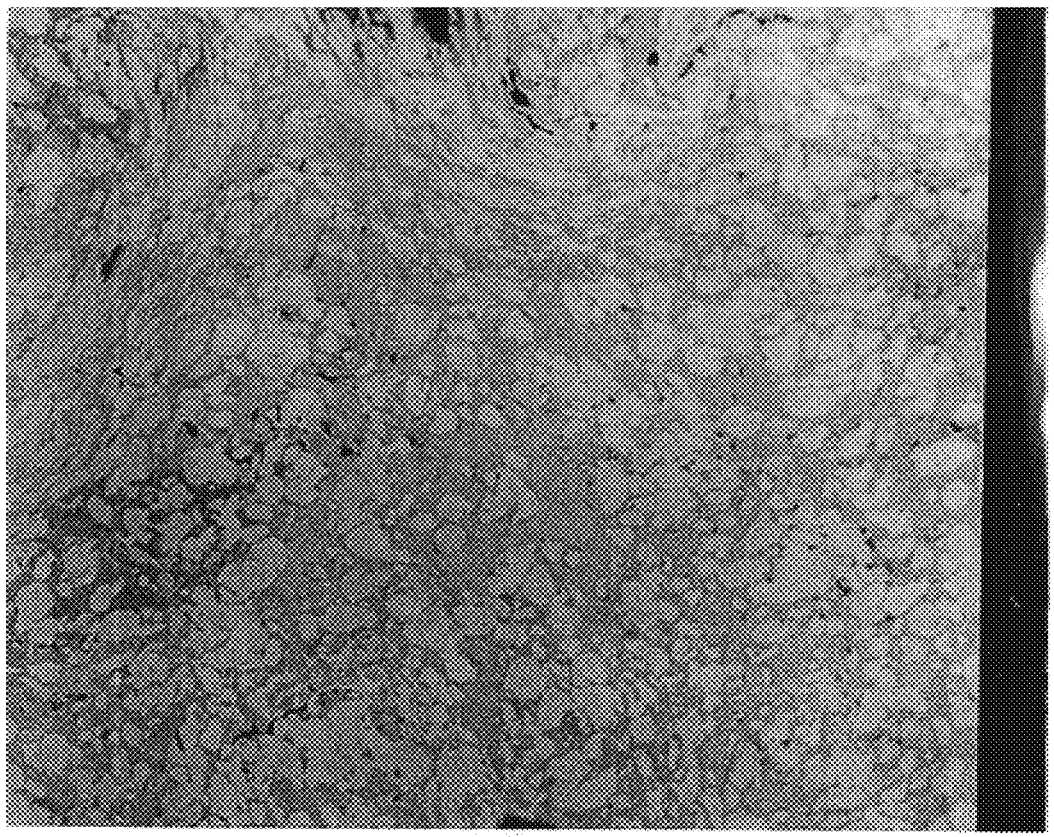
FIG. 5 is a micrograph of a hand consolidated sample described in Example 3, the white areas represent the residual Sn, the gray areas the intermetallic compound formed at the Sn—Ag interface.

FIG. 5 is a micrograph of a sample that had been hand consolidated using common dental office tools. The light areas represent the residual elemental Sn particles which are embedded in the gray matrix consisting of the intermetallic compound that was formed at the Sn—Ag interfaces.

Example 4

A solution of 20 g/l of $AgNO_3$ in 10% $HBF_4$ was prepared. 6.1 g of atomized, average size 13.5 μm diameter Ag—Sn compound powder was added to and stirred in the solution at room temperature for 6 min. The nominal composition of the atomized Ag—Sn alloy was 73 weight % Ag and 27 weight % Sn corresponding to the $Ag_3Sn$ compound composition. However, as a result of fast cooling during the atomization process, the atomized spherical particles were not in a thermodynamic equilibrium state and contained some elemental Sn. The powder was allowed to settle in the liquid which was removed from above the slurry. The slurry was rinsed in a 10% $HBF_4$ solution and again the liquid removed. Some of the slurry was consolidated by compression at 1,178 MPa in a steel mold.

Figure 6B:
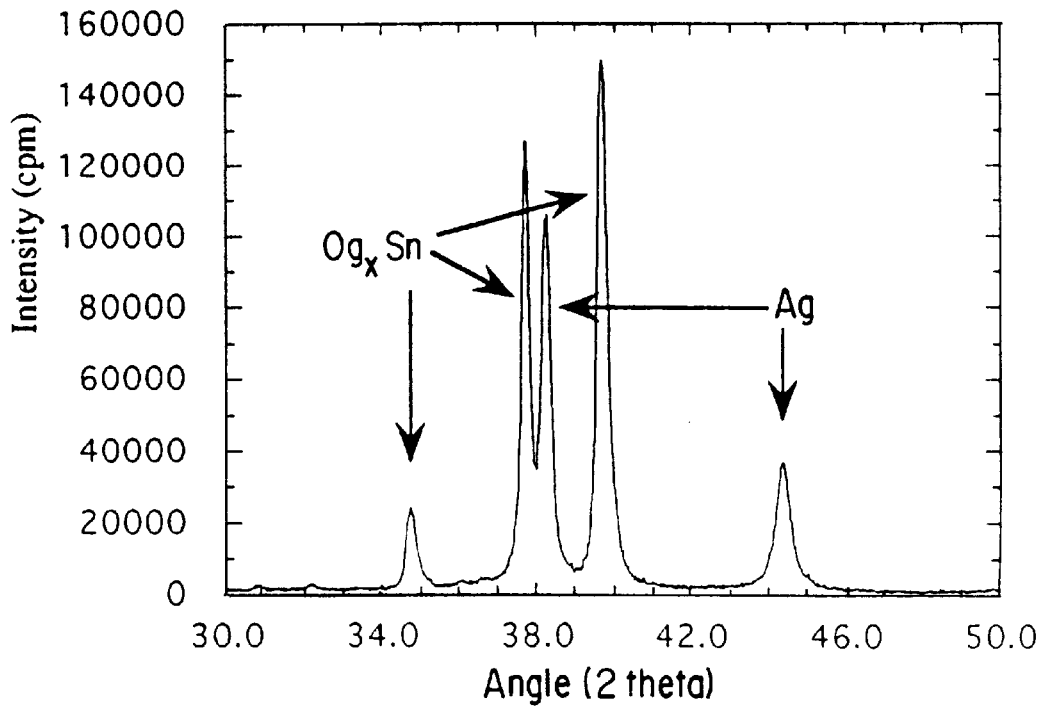
FIG. 6 are x-ray diffraction patterns of a Ag-coated nearly stoichiometric $Ag_3Sn$ powder (Example 4) taken at different times after consolidation. Spectrum 6a was taken after consolidation, spectrum 6b, 64 h later. The sample was kept at 37° C.
Figure 6A:
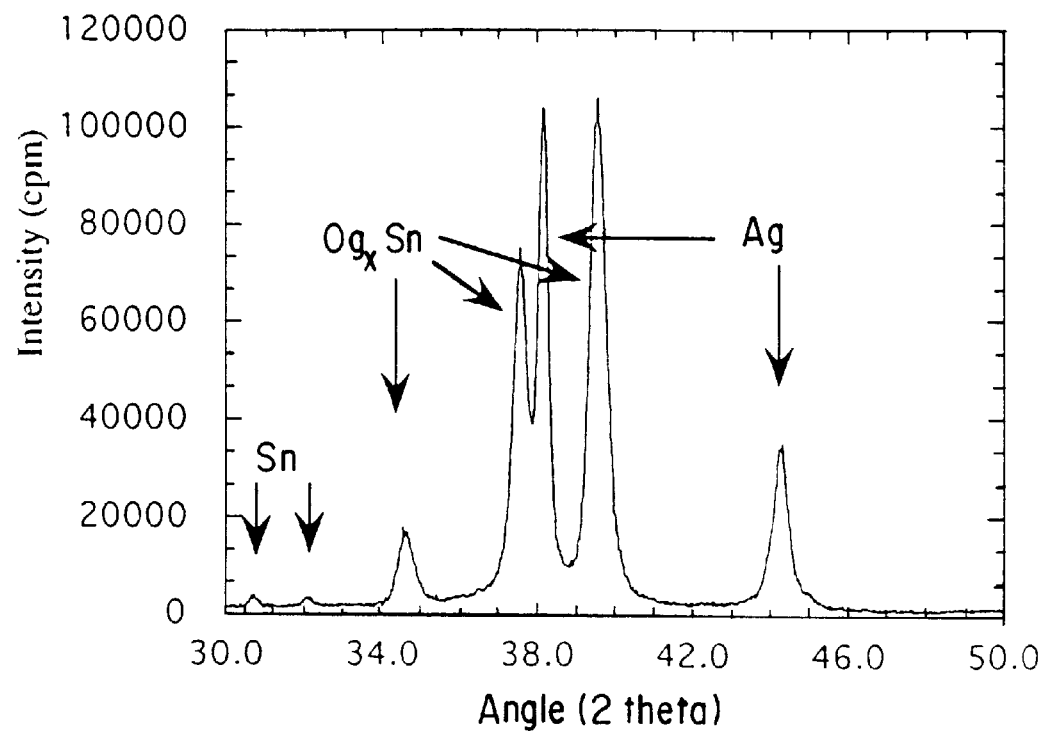

The diffraction pattern of the compressed sample, FIG. 6a reveals approximately equal amounts of elemental Ag and of the $Ag_3Sn+Ag_4Sn$ compounds and some traces of elemental Sn. FIG. 6b shows the diffraction spectrum of the same sample after 64 h at 37° C. This spectrum shows increased intensity of the diffraction lines corresponding to the compound, decrease of the Ag lines and almost complete disappearance of the diffraction lines of elemental Sn.

Figure 7:
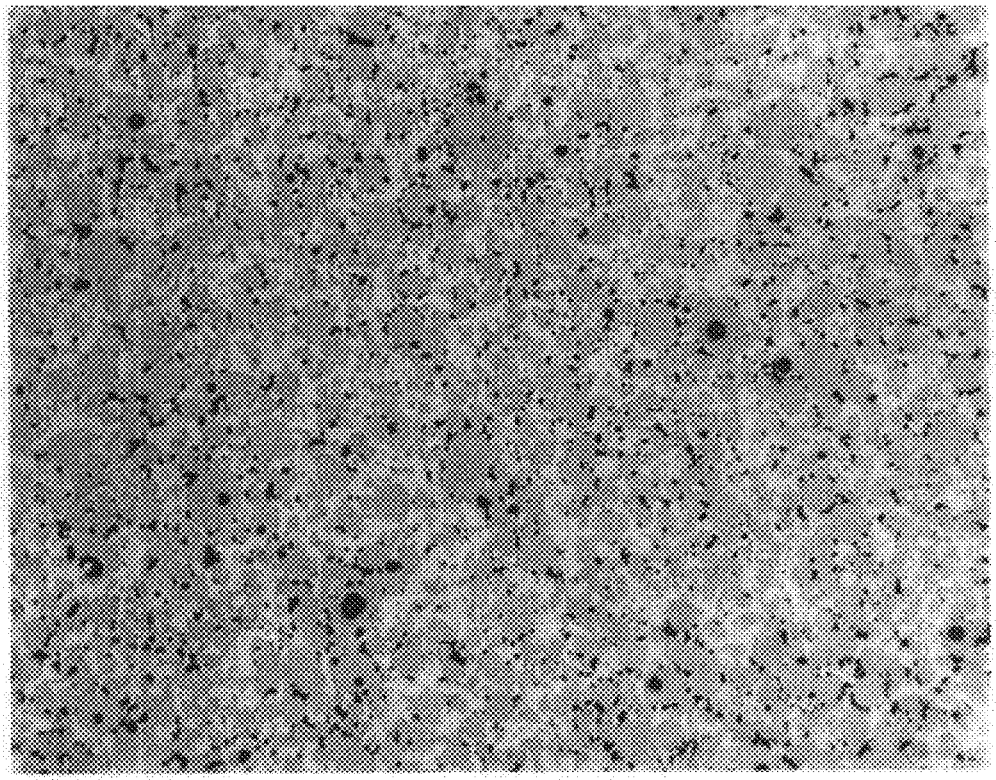
FIG. 7 is a micrograph of the sample described in Example 4, the white areas represent excess Ag, the gray areas represent mainly initial spherical intermetallic compound particles and also the additional compound formed at the Ag—$Ag_3Sn$ interface.

FIG. 7 is a metallographic cross-section of a hand consolidated sample, showing a uniform dispersion of the dark gray (the compound) phase and light (elemental) silver. The spherical shape of the initial pre-alloyed Ag—Sn compound particles is retained in most cases.

Example 5

A solution of 12 g/L $AgBF_4$ (Aldrich, Cat. No. 20,836-1) in 20% $HBF_4$ was prepared. An amount of 6.1 grams of atomized Ag—Sn alloy powder was stirred in the solution, for 5 min. The nominal composition of the alloy was 60 weight % Ag and 40 weight % Sn, corresponding to the two phase region, $Ag_3Sn+Sn$ in the Ag—Sn phase diagram. In other words, the alloy contained a certain fraction (≈18%) of excess Sn. The powder was allowed to settle, the liquid removed and the remaining slurry rinsed in a 10% $HBF_4$ solution. Again the powder was allowed to settle and the slurry removed. A pellet was pressed at 1,178 MPa from that slurry in a steel mold.

Figure 8A:
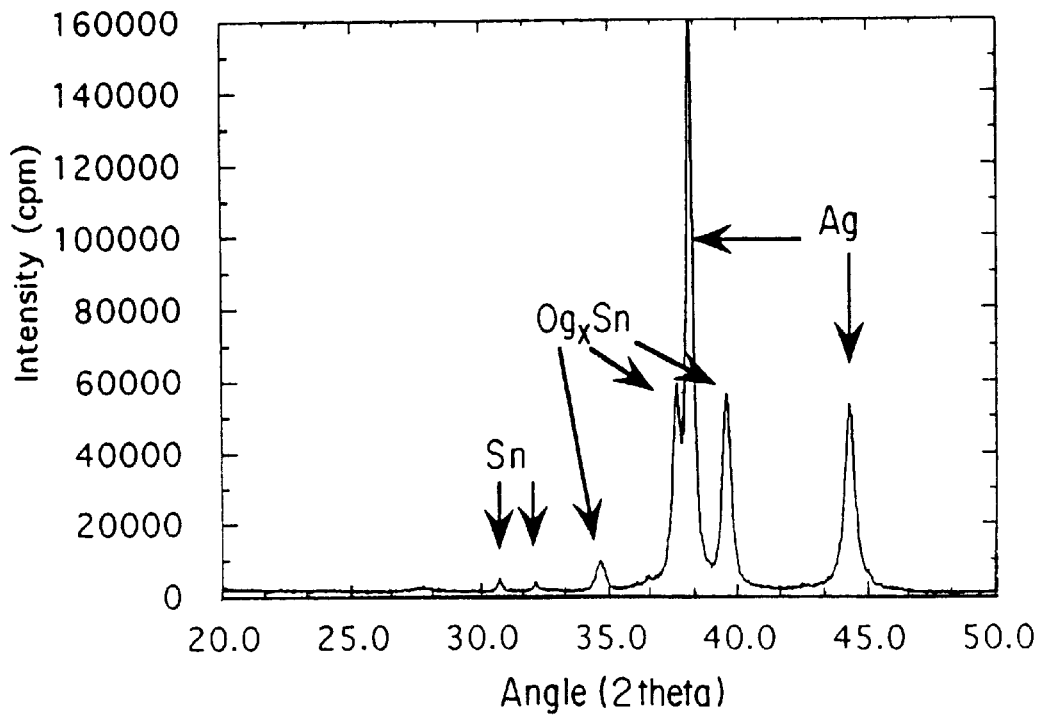
FIG. 8 are x-ray diffraction patterns of a consolidated Ag-coated atomized Ag—Sn alloy powder sample (Example 5). The initial composition of the alloy was 60 wt. % Ag and 40 wt. % Sn, namely a two phase, $Ag_3Sn$ and Sn alloy. Spectrum 8a was taken 19 h after consolidation and spectrum 8b, 119 h later.
Figure 8B:
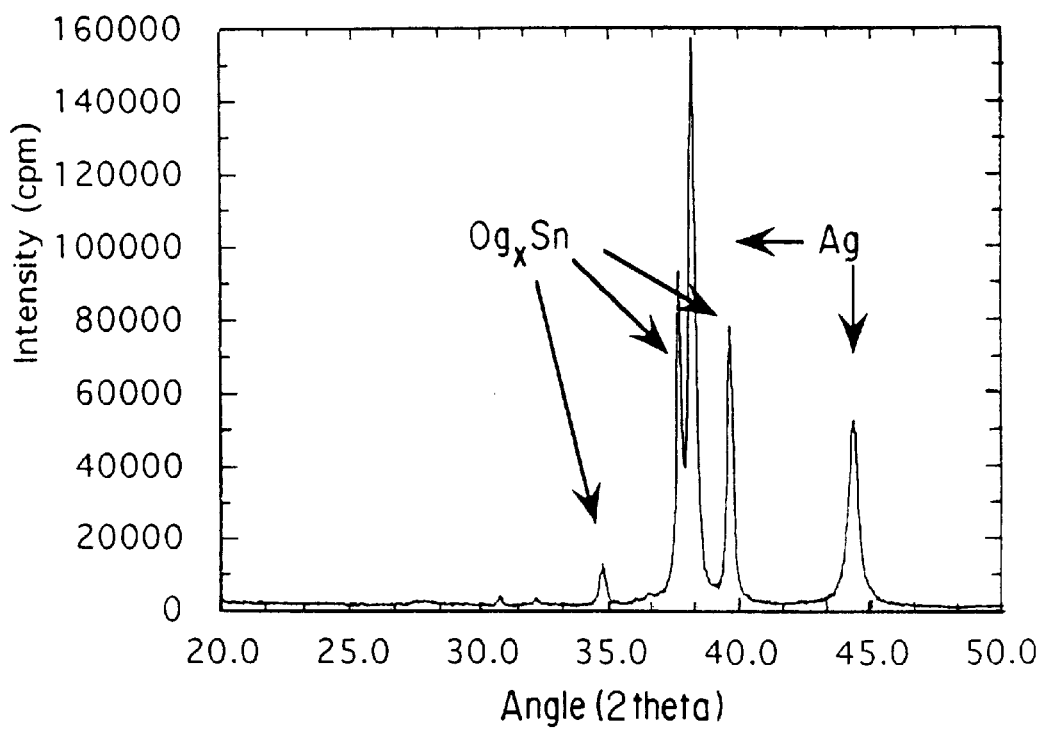
Figure 9:
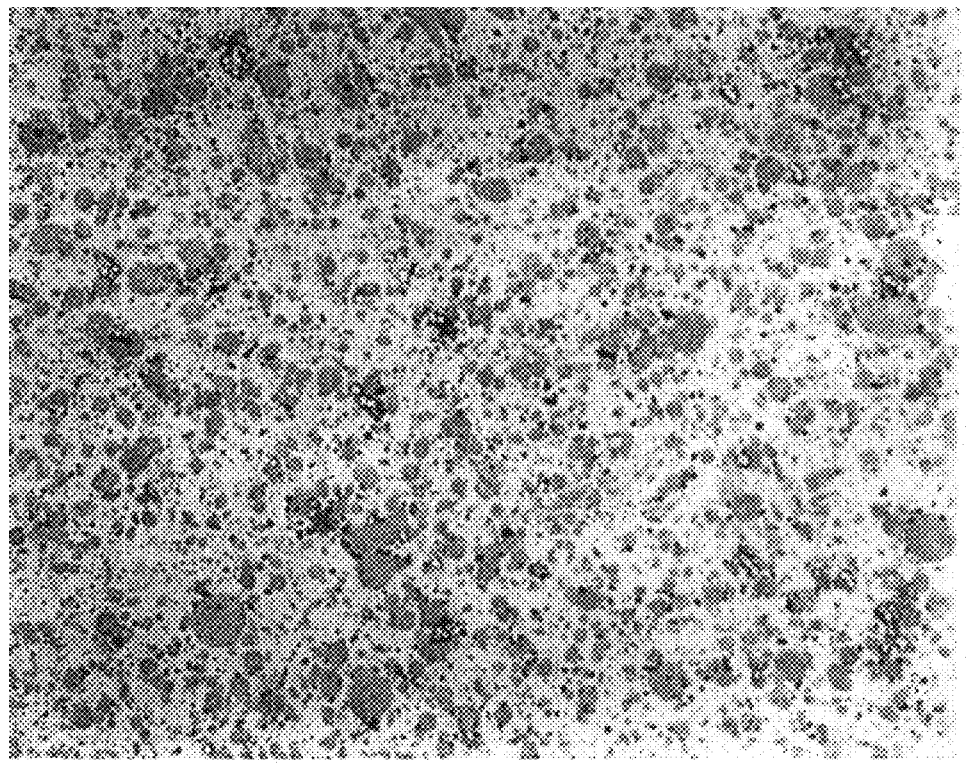
FIG. 9 is a micrograph of the sample described in Example 5, the white areas represent excess Ag, the gray areas represent mainly initial spherical intermetallic compound particles and also additional compound formed at the Ag—$Ag_3Sn$ interface.

The x-ray diffraction pattern of this sample taken after it had been kept for 19 h at room temperature, is shown in FIG. 8a and reveals the presence of elemental Ag (≈65%), $Ag_3Sn$ compound (≈35%) and traces of elemental Sn. The diffraction pattern of the sample, after it had been kept at 37° C. for 119 h, is shown in FIG. 8b. One observes a significant increase of the intensity of lines corresponding to the $Ag_3Sn$ compound, decrease of the intensity of the Ag lines, and a little change in the very low intensity of lines corresponding to the residual free Sn. Again, holding the sample at 37° C. induced a significant narrowing of the diffraction lines corresponding to the intermetallic compound $Ag_3Sn$. The metallography of a hand consolidated sample by common dental tools, shown in FIG. 9, shows a structure similar to that shown in FIG. 5, but with a higher $Ag/Ag_3Sn$ ratio. The gray areas represent the original Ag—Sn alloy particles which are embedded in the bright matrix consisting mainly of silver and silver-rich tin solid solution.

Example 6

Figure 10B:
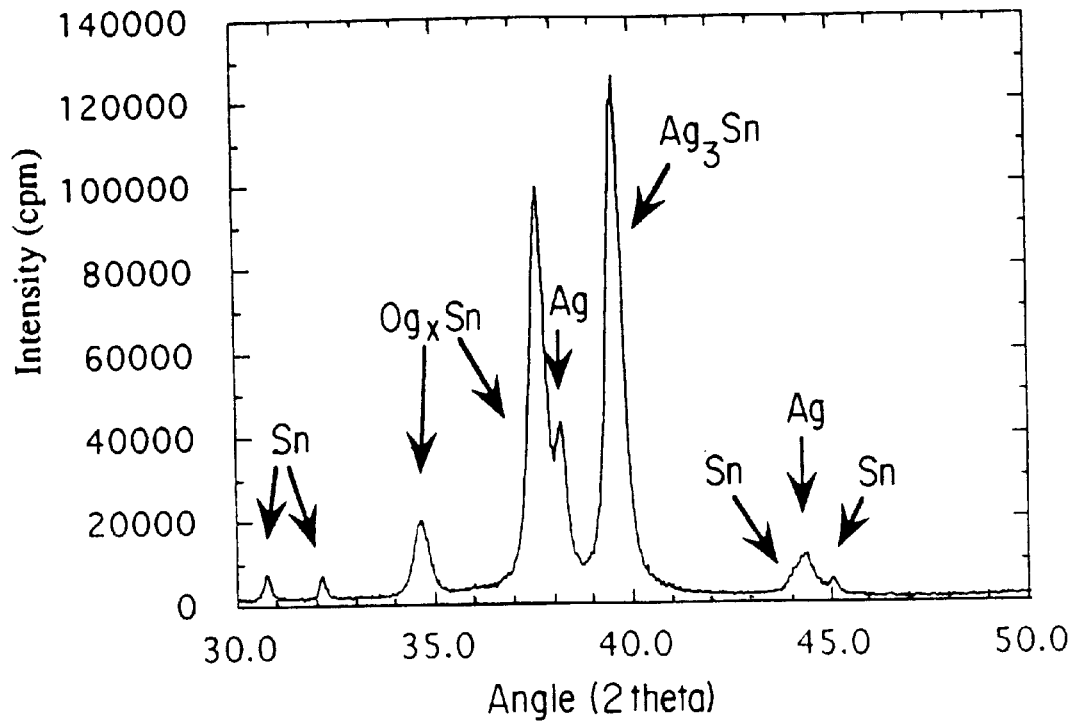
FIG. 10b shows an x-ray diffraction pattern of the sample having undergone a procedure according to the present invention.
Figure 10A:
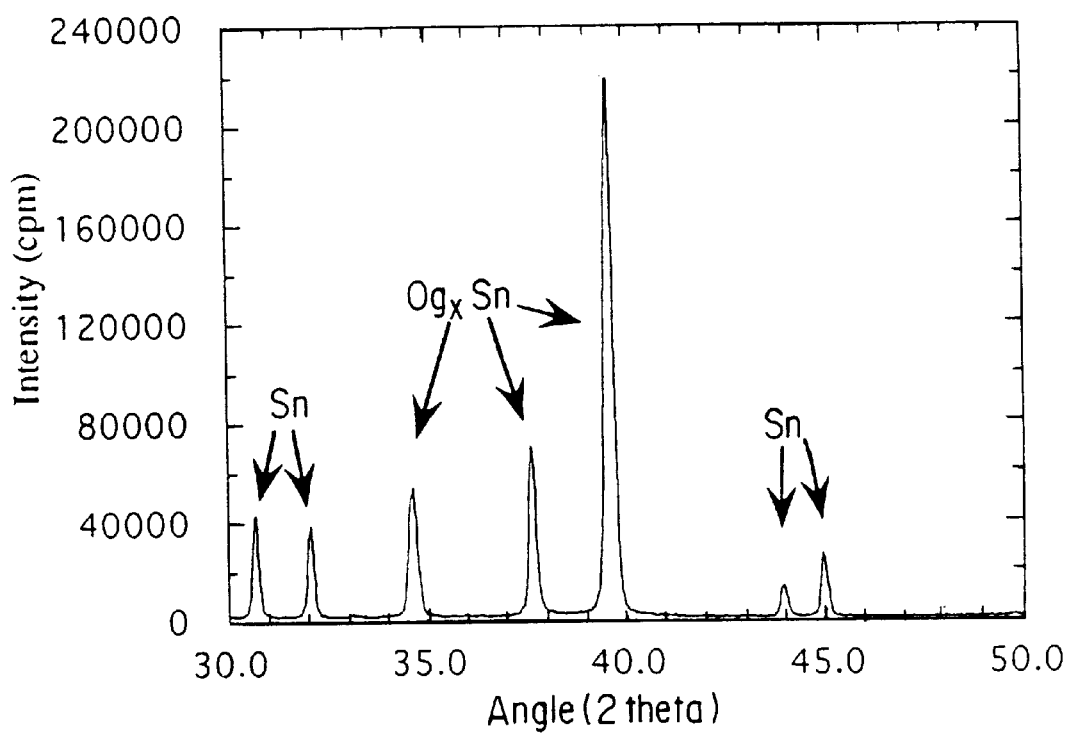
FIG. 10a shows the diffraction pattern of the initial Ag—Sn alloy, prior to coating.

A solution of 265 g/L KI (potassium iodide, ALFA Cat. #11601) and 10 g/L $AgNO_3$ (silver nitrate, ALFA Cat. #11414) was prepared. The pH=1.0 was adjusted by HCl and KOH. 4.06 g of Ag—Sn atomized alloy powder (13.2 μm average size) were rinsed in 10% $HBF_4$, and stirred in the first solution for 32 min. The nominal composition of the alloy was 60 weight % Ag and 40 weight % Sn, corresponding to the two phase region, $Ag_3Sn+Sn$ in the Ag—Sn phase diagram. In other words, the alloy contained a certain fraction (≈18%) of elemental Sn. The powder was allowed to settle, the solution was decanted and the slurry was rinsed three times in a solution of 2% KI. The solution was decanted and the slurry rinsed in water, the water was decanted and the slurry rinsed in a 10% $HBF_4$ solution. A pellet was prepared from the slurry by compressing in a steel mold at 1,178 MPa. The consolidated sample was examined by x-ray diffraction 24 h after the initial treatment. The results are shown in FIG. 10. FIG. 10a, is the diffraction pattern of the initial Ag—Sn alloy, prior to coating, showing the presence of the intermetallic compound $Ag_4Sn+Ag_3Sn$ and of elemental Sn. FIG. 10b, shows the x-ray diffraction pattern of the sample having undergone the procedure described in this example. The diffraction lines corresponding to the elemental Sn decrease to a low fraction of their initial value, diffraction peaks corresponding to elemental silver are present in the patterns and the diffraction peaks of the intermetallic compound broaden considerably. The broadening is due to the formation of additional $Ag_3Sn+Ag_4Sn$ compounds by means of the interdiffusion reaction of Ag with the free Sn. As mentioned previously, both intermetallic compounds exist over a range of compositions that corresponds to a range of lattice parameters, giving rise to the broadened diffraction lines.

Figure 11:
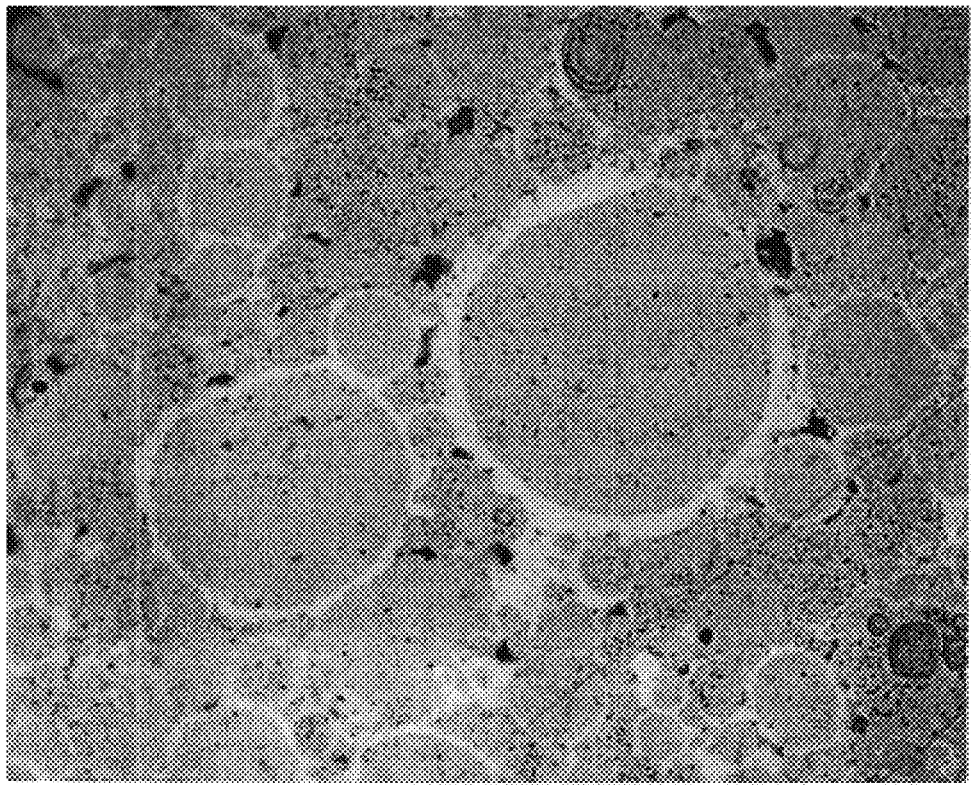
FIG. 11 is a micrograph of the sample prepared according to he method described in Example 6 that yields silver-coated $Ag_3Sn$ particles. There is continuous bright Ag coating surrounding each, (mostly spherical), well defined Ag—Sn alloy particles. The black dots are etch pits located at the excess free Sn sites. Some pores are also visible at the junction points of several particles.

FIG. 11 is an optical micrograph of a pellet of that slurry, compressed at 470 MPa, illustrating the efficiency of the process, described in this example, in producing with a relatively low volume fraction of silver (represented by the bright circular halos, surrounding the spherical, atomized Ag—Sn alloy particles), large silver—silver interface area that promotes consolidation, and silver-tin interface that promotes compound formation.

Example 7

A silver coating solution was prepared by dissolving 265 g of KI (ACS, ALFA Cat. #11601) and 10 g of $AgNO_3$ (ACS, ALFA Cat. #11414, 99.94% pure) and 8 ml concentrated HCl (Mallinckrodt) in 1 L of distilled $H_2O$ at pH 1.06 after adjustment by 10 M KOH. An amount of 4 g atomized Ag(60)Sn(40) powder with 13.2 μm average particle size was stirred in 500 ml of 10% $HBF_4$ solution for 30 sec. The acid was decanted and the wet powder rinsed in distilled $H_2O$. The powder was stirred in 500 ml of the silver coating solution for 30 min. After the slurry settled down, the solution was decanted and the slurry rinsed in 2% KI solution four consecutive times and finally rinsed with distilled $H_2O$. An amount of 0.81 g of Ag(70)Cu(30) atomized powder, 11.5 μm average size, 3.00 g of Ag powder, 4–7 μm size, 99.9% (ALFA Cat.#11402) and 1.48 g Ag powder, 1–3 μm, 99.9% (ALFA Cat.#11405) were mixed with the silver coated Ag(60)Sn(40) wet powder in 500 mL of 10% $HBF_4$. The slurry after decantation was consolidated in a steel mold at 471 MPa.

FIG. 12 is a metallography of the consolidated sample. The silver copper alloy component was added to increase the overall hardness of the consolidated solid.

Example 8

A solution of 21.7 g/L $AgBF_4$ (Ag as metal 12 g) (Aldrich, Cat. No. 20,836-1) in 5% $HBF_4$ was prepared. An amount of 7 g of In metal powder, ~400 mesh particle size, (ALFA, 99.99%, Cat. #11024) was stirred for 8 min in 250 ml of the silver fluoroborate solution at a pH of 0.5 and 23° C. temperature. The slurry, after decanting the solution, was rinsed in 10% $HBF_4$ and consolidated at 300 MPa in a steel mold.

Figure 13:
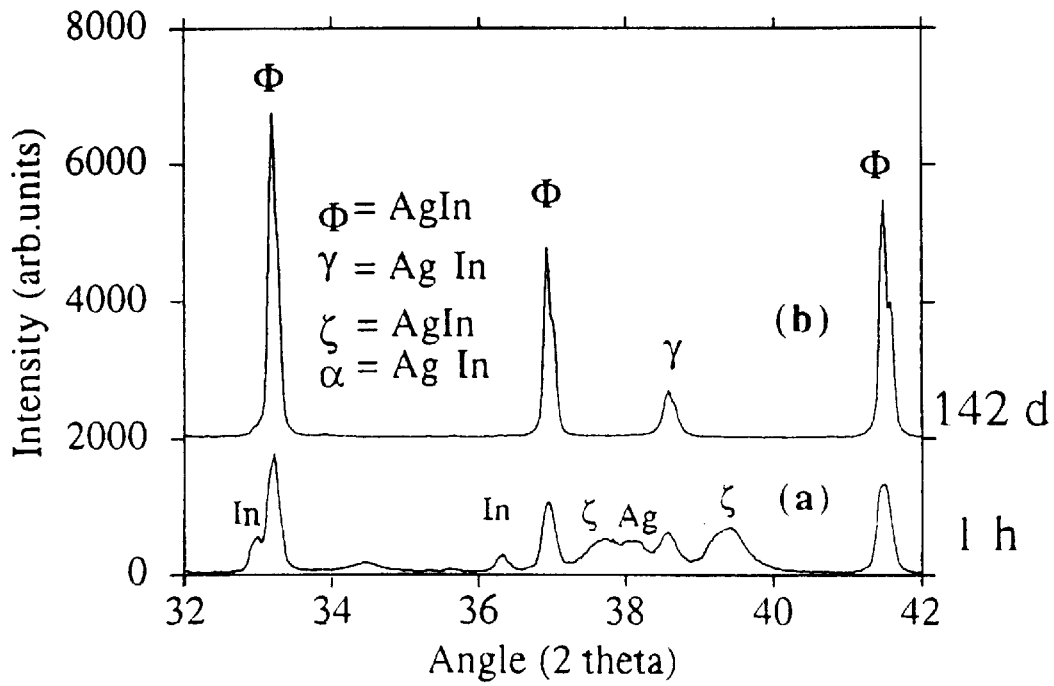
FIG. 13 shows the diffraction patterns of a consolidated mixture of indium particles immersion coated with silver (Example 8). (a) 1 h after consolidation wherein the sample consists of a multi-mixture of phases, $AgIn_2$, Φ-phase, ζ-phase, stable under equilibrium conditions mostly at elevated temperature, excess In and the solid solution of In in Ag. (b) after a lengthy (142 d) stay at room temperature wherein the sample consists of approximately 90% Φ-phase and 10% $Ag_9In_4$, γ-phase.

In FIG. 13, curve (a) is the x-ray diffraction pattern of the resulting disc, obtained approximately 1 h after the removal of the slurry from the solution. Analysis of the pattern obtained at this stage shows that the compound $AgIn_2$ (Φphase) is the main constituent with some additional $Ag_9In_4$ (γ phase), AgIn (ζ phase), an Ag based phase (a solid solution) and an In-based phase. Curve (b) shows the x-ray pattern obtained from the same sample after an anneal of 142 d at ambient temperature. The relative intensity of the diffraction lines indicated that the $AgIn_2$ is the main constituent, making up approximately 90% of the material.

Example 9

Gold chloride (AuCl) was prepared by dissolving metallic gold in aqua regia and evaporating the solution. An amount of 2.65 g gold chloride (AuCl) was dissolved in 250 ml 10% fluoroboric ($HBF_4$) acid at pH=0.2, and 23° C. An amount of 4.03 g of Sn powder, 1–5 μm particle size was added to 250 ml solution and stirred for 30 min. The solution was decanted in the slurry rinsed in 10% $HBF_4$.

Figure 14:
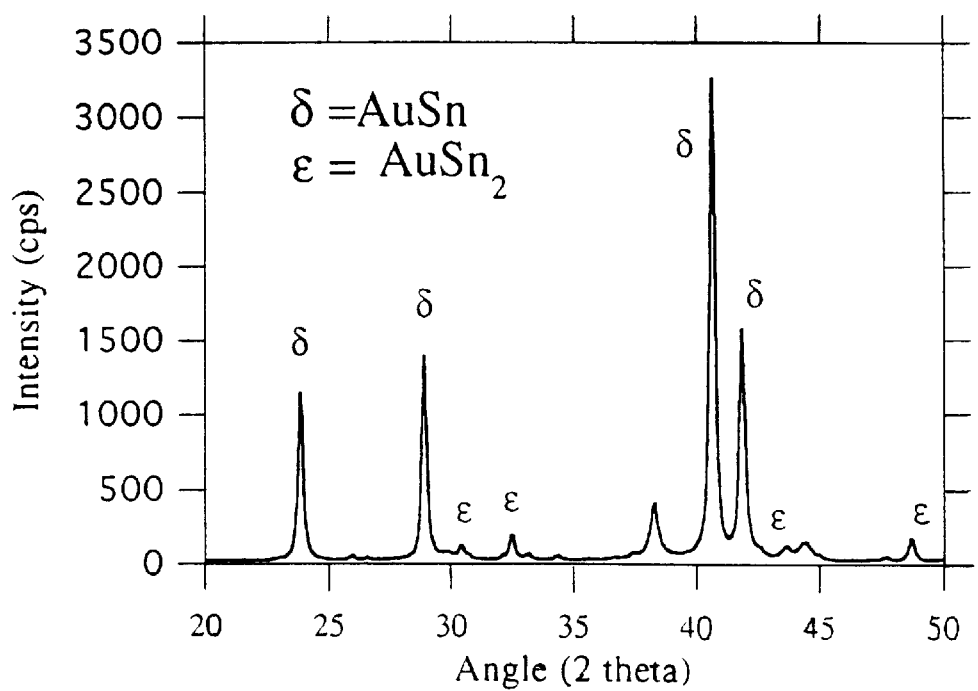
FIG. 14 shows diffraction patterns of a consolidated mixture of tin particles immersion coated with gold (Example 9). The sample consists essentially of the δ-AuSn compound, a small fraction of $AuSn_2$, the ε-phase, and some excess Au.

FIG. 14 is a x-ray pattern of a disc made from the slurry that was removed from the solution consolidated at 1220 MPa. The x-ray exposure was made lh after the removal of the slurry from the solution. The sample consists mostly of the AuSn compound, a small fraction of $AuSn_2$ and some excess Au.

Example 10

Figure 15:
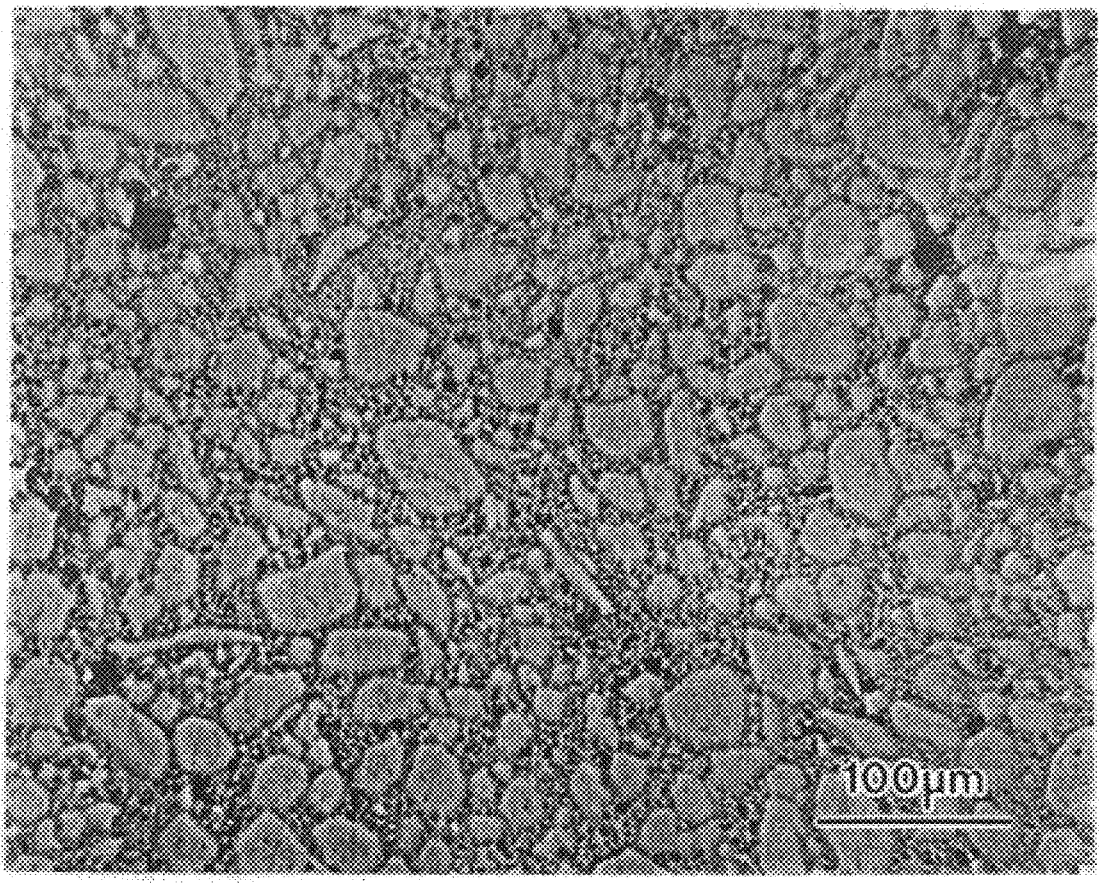
FIG. 15 is an optical micrograph of a Cu—W bi-phase composite, consolidated under dilute fluoroboric acid as described in Example 10.

A plating solution was prepared by dissolving 288 g of potassium pyrophosphate $K_4P_2O_7$ (ALFA, Johnson Matthey, Cat.#13436), 75 g of copper pyrophosphate $Cu_2P_2O_7 \cdot 3H_2O$ (ALFA, Johnson Matthey, Cat.#18220), 10 g potassium nitrate $KNO_3$ (J. T. Baker, Cat. #3190-1) and 5 ml of ammonium hydroxide $NH_4OH$ (Mallinckrodt, Cat. #1177) in 1000 ml of distilled water. The pH of the solution was adjusted by adding, ammonium hydroxide or potassium hydroxide to increase, phosphoric acid $H_3PO_4$ to decrease to pH=8.65. 175 ml of that solution (containing 4.7 g of copper as metal) were heated to 55° C. and 30.5 g of tungsten (W) particles, 2 to 28 μm size range added. The suspension was stirred until the Cu was exhausted as determined by the change of color of the solution. The time of processing was dependent on the particle size (surface area). The copper was exhausted within 15 minutes for 2 μm size tungsten particles and 60 minutes for 28 μm size particles. The liquid was decanted, the slurry rinsed several times in water and ethanol, and air dried. The dry powder was mixed with 2 vol % of fluoroboric acid ($HBF_4$) and compressed in steel molds at pressures in the 1500–1800 MPa range. FIG. 15 shows a micrograph of a sample that had been cold-pressed at 1200 MPa from a slurry removed from the solution. The density of this compact was 88±2% of theoretical density.

Example 11

A solution of 29.4 g/L $AgBF_4$ (16.2 g Ag as metal) (Aldrich, Cat. No. 20,836-1) in 5% $HBF_4$ was prepared. An amount of 3.15 g of In metal powder, ~400 mesh particle size, (ALFA, 99.99%, Cat. #11024) was stirred for 10 min in 250 ml of the silver fluoroborate solution at a pH of 0.5 and 23° C. temperature. The slurry, after decanting the solution, was rinsed in 10% $HBF_4$ and consolidated at 300 MPa in a steel mold.

An x-ray pattern of the resulting disc was obtained approximately 20 h after the removal of the slurry from the solution. Analysis of the pattern obtained shows that Ag is the main component with the additional presence of $AgIn_2$ (Φ phase), $Ag_9In_4$ (γ phase), and AgIn (ζ phase). The x-ray pattern after a 51 h anneal at 140° C. shows that $Ag_9In_4$ is the major constituent (75%) with $Ag_3In$ (25%) and some residual Ag and traces of $AgIn_2$.

Example 12

A solution of 708 g/L Cu(BF4)2 (Fidelity Chemical Products Corp. #0360) in 10% $HBF_4$ was prepared. Silver metal constituted 190 g of that amount of copper fluoroborate. An amount of 8 g of Sn metal powder, –325 mesh particle size, was stirred for 10 min in 100 ml of the copper added to 400 ml solution of 10% fluoroborate solution at a pH 0.2 and at 23° C. temperature. The slurry, after decanting the solution, was rinsed in 10% $HBF_4$ and consolidated at 300 MPa in a steel mold.

X-ray exposure was made within 1 h after the removal of the slurry from the solution. Analysis of the pattern obtained at this stage shows that Cu and Sn are the main components with some additional Cu$_3$Sn and Cu$_5$.6Sn (B'-phase) present. After aging for 69 H at 150° C., the sample consists of mixture of Cu and Cu$_3$Sn and traces of another phase.

While the invention has been illustratively described herein with reference to various preferred features, aspects and embodiments, it will be appreciated that the invention is not thus limited, and may be widely varied in respect of alternative variations, modifications, and other embodiments, and therefore the invention is to be broadly contrued as including such alternative variations, modifications and other embodiments, within the spirit and scope of the invention claimed.

What is claimed is:

1. A process for consolidating a powder, particulate, sheet or foil of at least one member selected from the group consisting of elemental metallic, metallic alloy and intermetallic compounds having surface oxides, the process comprising:

coating the powder, particulate, sheet or foil with an oxide replacing metal by immersing said powder, sheet or foil in a solution containing an electrolyte, said electrolyte selected from the group consisting of fluoroborate, sulfamate, iodide, cyanide, nitrate, pyrophosphate and sulfide salts of the oxide-replacing metal and mixtures thereof;

separating the coated powder, particulate, sheet, or foil from the electrolyte solution;

treating the coated powder, particulate, sheet, or foil with a solution consisting essentially of an acid selected from the group consisting of acetic acid, fluoroboric acid, sulfuric acid, fluoric acid, citric acid, adipic acid, ascorbic acid and nitric acid; and consolidating the treated powder, particulate, sheet, or foil at near ambient temperature by compacting said treated powder, particulate, sheet or foil without amalgamating same.

2. The process according to claim 1, wherein the oxide-replacing metal is selected from the group consisting of Au, Ag, Fe, Pt, Pd, Ni, Co and Cu.

3. The process according to claim 1, wherein the elemental metallic is selected from the group consisting of Ga, Ir, La, Re, Rh, Ru, Sn, Ti, Y, Zn, Nb, Mo, Ta, Sc, Hf, Ce, Pr, Nd, Sm, Gd, Tb, Sy, Ho, Er, Tm, Yb, Lu, U and W.

4. The process according to claim 3, wherein the oxide replacing metal is Cu, the elemental metallic is W and the electrolyte is copper pyrophosphate.

5. The process according to claim 3, wherein the oxide replacing metal is Ni and the elemental metallic is Ti.

6. The process according to claim 1, wherein the intermetallic compound is comprised of at least one first elemental metal being a matrix species, and at least one second elemental metal being a fast diffusing species which is able to diffuse into the interstitial space of the matrix species.

7. The process according to claim 1, wherein the powder comprises atomized, spherical particles having an equiaxial particle size of from about 0.5 $\mu$m to about 50 $\mu$m.

8. The process according to claim 1, wherein the powder comprises a mixture of (1) a silver-tin compound selected from the group consisting of a pre-alloyed Ag$_3$Sn and a pre-alloyed Ag$_4$Sn, and (2) at least two elemental metallic powders.

9. The process according to claim 1, wherein the powder further comprises a reinforcing structural particulate or fiber additive.

10. The process according to claim 9, wherein the structural particulate or fiber additive is selected from the group consisting of alumina powder, silicon carbide, graphite, diamond, sapphire and combinations thereof.

11. The process according to claim 1, wherein the acid is fluoroboric acid.

12. The process according to claim 1, wherein the concentration of the acid is from about 1% to about 30%.

13. A process according to claim 1, wherein said powder, particulate, sheet, or foil is consolidated in an acidic solution.

14. A process for synthesizing bulk intermetallics or homogeneously distributed two-phase alloys comprising:

generating an interface between as first powder of a less noble element and a second more noble element by dissolving the second element in an electrolyte, immersing the first powder element in the electrolyte, allowing the second element to deposit from the electrolyte onto the first powder element;

allowing the first powder element and the second element to form an intermetallic compound or a homogeneously distributed two-phase alloy at or about ambient temperature;

separating the coated powder from the electrolyte solution;

treating the coated powder with a solution consisting essentially of an acid selected from the group consisting of acetic acid, fluoroboric acid, sulfuric acid, fluoric acid, citric acid, adipic acid, ascorbic acid and nitric acid; and consolidating the treated powder without amalgamating same.

15. The process according to claim 14, wherein the first element is selected from the group consisting of Sc, Y, Ln, Ti, Zr, Th, U, Np and Pu and the second element is selected from the group consisting of Fe, Co, Ni, Pd and Pt.

16. The process according to claim 15, further comprising controlling concentration of electrolyte, amounts of electrolyte solution and solid component and time-duration of the immersion so as to control composition ratio of the intermetallic formed.

17. The process according to claim 14, wherein the first element is selected from the group consisting of Nb, Mo, Ta and W and the second element is selected from the group consisting of Cu, Ag and Au.

18. The process according to claim 17, wherein a homogeneously dispersed two-phase alloy is formed.

19. The process according to claim 14, wherein the first element is selected from the group consisting of In, Ti, Sn and Pb and the second element is selected from the group consisting of Pd, Cu, Ag and Au.

20. The process according to claim 19, further comprising adding a chemically inert fine dispersion component to the electrolye thereby forming a metal matrix component wherein the chemically inert component is homogeneously dispersed in the matrix.

21. The process according to claim 20, wherein the chemically inert fine dispersion component is selected from the group consisting of alumina powder, silicon carbide, graphite, diamond, sapphire and combinations thereof.

22. The process according to claim 19, further comprising controlling concentration of electrolyte, amounts of electrolyte solution and solid component and time-duration of the immersion so as to control composition ratio of the two phase alloy formed.

23. The process according to claim 14, wherein a two phase alloy is formed and the first element is aluminum and the second element is selected from the group consisting of Zn, Sn, Cr, Fe and Ni.

24. The process according to claim 14, further comprising applying axial pressure or injection molding to consolidate the bulk intermetallic or two-phase alloy into near net shape.

* * * * *